US012642973B2

(12) United States Patent

Mower

(10) Patent No.: US 12,642,973 B2

(45) Date of Patent: Jun. 2, 2026

(54) METHOD AND APPARATUS FOR INTRACHAMBER RESYNCHRONIZATION

(71) Applicant: MIROWSKI FAMILY VENTURES, LLC, Washington, DC (US)

(72) Inventor: Morton M. Mower, Denver, CO (US)

(73) Assignee: MIROWSKI FAMILY VENTURES, LLC, Washington, DC (US)

( * ) Notice: Subject to any disclaimer, the term of this patent is extended or adjusted under 35 U.S.C. 154(b) by 142 days.

(21) Appl. No.: 17/543,917

(22) Filed: Dec. 7, 2021

(65) Prior Publication Data

US 2022/0088384 A1 Mar. 24, 2022

Related U.S. Application Data

(63) Continuation of application No. 15/869,807, filed on Jan. 12, 2018, now Pat. No. 11,207,524, which is a (Continued)

(51) Int. Cl.
| | |
|---|---|
| *A61N 1/365* | (2006.01) |
| *A61N 1/362* | (2006.01) |
| *A61N 1/368* | (2006.01) |

(52) U.S. Cl.
CPC ....... *A61N 1/3627* (2013.01); *A61N 1/36592* (2013.01); *A61N 1/36842* (2017.08); *A61N 1/36843* (2017.08)

(58) Field of Classification Search
CPC .......................... A61N 1/3684; A61N 1/3627
See application file for complete search history.

(56) References Cited

U.S. PATENT DOCUMENTS

| | | | |
|---|---|---|---|
| 3,345,990 | A | 10/1967 | Berkovits |
| 3,431,912 | A | 3/1969 | Keller, Jr. |

(Continued)

FOREIGN PATENT DOCUMENTS

| | | |
|---|---|---|
| EP | 0017447 A1 | 10/1980 |
| EP | 0039269 A1 | 11/1981 |

(Continued)

OTHER PUBLICATIONS

"Effectiveness of bi-atrial pacing for reducing atrial fibrillation after coronary artery bypass graft surgery." EP Gerstenfeld , et al.; Department of Medicine, University of Mass. Medical Center; 2001.

(Continued)

*Primary Examiner* — Michael J D'Abreu
(74) *Attorney, Agent, or Firm* — Oblon, McClelland, Maier & Neustadt, L.L.P.

(57) ABSTRACT

Methods, apparatus, and systems are provided to control contraction of the heart. At least one sensing element receives signals indicating electrical activity of sinus rhythm of the heart. Based on the received signals, the progress of contraction of the heart is determined. Based on the progress of contraction, the chamber of the heart may then be stimulated at a plurality of locations. In another embodiment, a plurality of electrodes are implanted in the left ventricle to stimulate at multiple locations in the left ventricle for the purpose of improving hemodynamic performance and increasing cardiac output in a patient who is suffering from congestive heart failure.

12 Claims, 4 Drawing Sheets

Related U.S. Application Data continuation of application No. 14/206,111, filed on Mar. 12, 2014, now Pat. No. 9,901,739, which is a continuation of application No. 10/656,222, filed on Sep. 8, 2003, now abandoned.

(56) References Cited

U.S. PATENT DOCUMENTS

| | | | |
|---|---|---|---|
| 3,433,228 A | 3/1969 | Keller, Jr. | |
| 3,595,242 A | 7/1971 | Berkovits | |
| 3,648,707 A | 3/1972 | Greatbach | |
| 3,747,604 A | 7/1973 | Berkovits | |
| 3,814,106 A | 6/1974 | Berkovits | |
| 3,903,897 A | 9/1975 | Woolons et al. | |
| 3,937,226 A | 2/1976 | Funke | |
| 4,052,991 A | 10/1977 | Zacouto | |
| 4,057,067 A | 11/1977 | Lajos | |
| 4,088,140 A | 5/1978 | Rockland et al. | |
| 4,303,075 A | 12/1981 | Heilman et al. | |
| 4,312,355 A | 1/1982 | Funke | |
| 4,332,259 A | 6/1982 | Mccorkle, Jr. | |
| 4,335,727 A | 6/1982 | Mcpherson | |
| 4,354,497 A | 10/1982 | Kahn | |
| 4,378,020 A | 3/1983 | Nappholz et al. | |
| 4,386,610 A | 6/1983 | Leckrone | |
| 4,401,119 A | 8/1983 | Herpers | |
| 4,418,695 A | 12/1983 | Buffet | |
| 4,429,697 A | 2/1984 | Nappholz et al. | |
| 4,452,248 A | 6/1984 | Keller, Jr. | |
| 4,458,677 A | 7/1984 | Mccorkle, Jr. | |
| 4,541,417 A | 9/1985 | Krikorian | |
| 4,548,203 A | 10/1985 | Tacker, Jr. et al. | |
| 4,554,922 A | 11/1985 | Prystowsky et al. | |
| 4,559,946 A | 12/1985 | Mower | |
| 4,561,442 A | 12/1985 | Vollmann et al. | |
| 4,624,260 A | 11/1986 | Baker, Jr. et al. | |
| 4,628,934 A | 12/1986 | Pohndorf et al. | |
| 4,641,656 A | 2/1987 | Smits | |
| 4,685,446 A | 8/1987 | Choy | |
| 4,705,043 A | 11/1987 | Imran | |
| 4,712,555 A | 12/1987 | Thornander et al. | |
| 4,727,877 A | 3/1988 | Kallok | |
| 4,774,950 A | 10/1988 | Cohen | |
| 4,790,317 A | 12/1988 | Davies | |
| 4,799,486 A | 1/1989 | Dufault | |
| 4,817,608 A | 4/1989 | Shapland et al. | |
| 4,827,932 A | 5/1989 | Ideker et al. | |
| 4,827,934 A | 5/1989 | Ekwall | |
| 4,830,006 A | 5/1989 | Haluska et al. | |
| 4,925,443 A | 5/1990 | Heilman et al. | |
| 4,928,688 A | 5/1990 | Mower | |
| 4,932,407 A | 6/1990 | Williams | |
| 4,958,632 A | 9/1990 | Duggan | |
| 4,967,749 A | 11/1990 | Cohen | |
| 4,974,588 A | 12/1990 | Smits | |
| 4,998,975 A | 3/1991 | Cohen et al. | |
| 5,014,696 A | 5/1991 | Mehra | |
| 5,024,222 A | 6/1991 | Thacker | |
| 5,083,563 A | 1/1992 | Collins | |
| 5,099,838 A | 3/1992 | Bardy | |
| 5,111,811 A | 5/1992 | Smits | |
| 5,129,394 A | 7/1992 | Mehra | |
| 5,158,097 A | 10/1992 | Christlieb | |
| 5,165,403 A | 11/1992 | Mehra | |
| 5,174,289 A | 12/1992 | Cohen | |
| 5,213,098 A | 5/1993 | Bennett et al. | |
| 5,251,621 A | 10/1993 | Collins | |
| 5,318,593 A | 6/1994 | Duggan | |
| 5,334,222 A | 8/1994 | Salo et al. | |
| 5,385,579 A | 1/1995 | Helland | |
| 5,403,356 A | 4/1995 | Hill et al. | |
| 5,487,758 A | 1/1996 | Hoegnelid et al. | |
| 5,545,204 A | 8/1996 | Cammilli et al. | |
| 5,551,427 A | 9/1996 | Altman | |
| 5,584,868 A | 12/1996 | Salo et al. | |
| 5,626,620 A | 5/1997 | Kieval et al. | |
| 5,728,140 A | 3/1998 | Salo et al. | |
| 5,755,766 A | 5/1998 | Chastain et al. | |
| 5,800,464 A * | 9/1998 | Kieval | A61N 1/3622 |
| | | | 607/9 |
| 5,800,465 A | 9/1998 | Thompson et al. | |
| 5,814,079 A | 9/1998 | Kieval | |
| 5,899,930 A | 5/1999 | Flynn et al. | |
| 5,902,324 A | 5/1999 | Thompson et al. | |
| 5,919,209 A | 7/1999 | Schouten | |
| 5,935,160 A | 8/1999 | Auricchio et al. | |
| 6,185,459 B1 | 2/2001 | Mehra et al. | |
| 6,233,484 B1 * | 5/2001 | Ben-Haim | A61N 1/3628 |
| | | | 607/9 |
| 6,298,268 B1 | 10/2001 | Ben-Haim et al. | |
| 6,317,631 B1 | 11/2001 | Ben-Haim et al. | |
| 6,330,476 B1 | 12/2001 | Ben-Haim et al. | |
| 6,337,995 B1 | 1/2002 | Mower | |
| 6,343,232 B1 | 1/2002 | Mower | |
| 6,421,564 B1 | 7/2002 | Yerich et al. | |
| 6,463,324 B1 | 10/2002 | Ben-Haim et al. | |
| 6,473,645 B1 | 10/2002 | Levine | |
| 6,556,874 B2 | 4/2003 | Audoglio | |
| RE38,119 E | 5/2003 | Mower | |
| 6,567,700 B1 | 5/2003 | Turcott et al. | |
| 6,584,362 B1 | 6/2003 | Scheiner et al. | |
| 6,628,988 B2 * | 9/2003 | Kramer | A61N 1/3627 |
| | | | 607/9 |
| 6,643,546 B2 * | 11/2003 | Mathis | A61N 1/36842 |
| | | | 607/148 |
| 6,937,895 B1 | 8/2005 | Lu | |
| 6,959,214 B2 | 10/2005 | Pape et al. | |
| 7,096,064 B2 | 8/2006 | Deno et al. | |
| 7,487,758 B1 | 2/2009 | Reid | |
| 2002/0082651 A1 | 6/2002 | Stahmann et al. | |
| 2002/0128688 A1 | 9/2002 | Stoop | |
| 2003/0105493 A1 | 6/2003 | Salo | |
| 2003/0105496 A1 | 6/2003 | Yu et al. | |
| 2007/0225765 A1 | 9/2007 | King | |

FOREIGN PATENT DOCUMENTS

| | | | |
|---|---|---|---|
| EP | 0 494 487 A2 | 1/1996 | |
| EP | 0 726 082 A2 | 8/1996 | |
| EP | 1 249 254 A2 | 10/2002 | |
| GB | 2119255 A | 7/1975 | |
| GB | 1401247 | 11/1983 | |
| WO | WO 82/03783 | 11/1982 | |
| WO | WO 86/05698 | 10/1986 | |

OTHER PUBLICATIONS

"Evaluation of bi-atrial pacing and single site right atrial pacing for the prevention of atrial fibrillation." Y. Enjoji, et al.; Third Dept. of Internal Medicine, Toho University School of Medicine; 2002.

"Bi-atrial mapping of atrial arrhythmias." R. Lemery; Division of Cardiology, Ottawa Heart Institute; 2002.

"Permanent atrial resynchronization by synchronous bi-atrial pacing in the preventive treatment of atrial flutter associated with high degree interatrial block." C. Daubert, et al.; Hote-Dieu, Rennes; 1994.

"Comparison Between Uni-Ventricular Pacing and Beventricular Pacing After AV Nodal Ablation on Systolic Function of Heart Failure Patients with Atrial Fibrillation." Angelo Auricchio, MD, PhD, et al. University Hosp., and Guidant Corp.

"The Influence of Intrinsic Conduction on Left Ventricular dP/dt During Biventricular Pacing in Cardiac Resynchronisation Therapy," Berry Van Gelder, PhD et al.; Catharina Hosp.

"Triple-Site Pacing in Patients with Biventricular Device, Incidence of the Phenomenon and Cardiac Resynchronization Benefit." Alan Bulava, MD et al.; Dept. of Cardiac Diseases, Rome.

"Feasibility of Adjusting Cardiac Resynchronization by Manipulating Left Ventricular Pacing Stimulus Strength." Usha Tedrow, MD, et al.; Brigham and Women's Hosp., Boston, MA.

"Multisite Right Ventricular Pacing: An Alternative Form of Cardiac Resynchronisation." Rebecca Lane, et al.; St. Mary's Hosp. and Imperial College School of Medicine, UK.

(56)                  References Cited

OTHER PUBLICATIONS

"The Influence of Lead Position and Interventricular Pacing Interval for Optimal Cardiac Resynchronisation Therapy." Rebecca Lane, et al.; St. Mary's Hosp. and Imperial College School of Medicine, UK.

Paced QRS Width Narrows with Increasing Pacing Voltages: Implications for Ventricular Resynchronization. Jesus Val-Mejias, MD, et al.; St. Francis Hosp., Wichita, KS.

"Disparity Between Left Ventricular and Biventricular Pacing Thresholds." Joon Ahn, MD; Emory Univ., Atlanta, GA.

"Intra-Left Ventricular Mechanical Asynchrony Is an Independent Predictive Factor of Heart Failure Worsening Regardless of the QRS Width and Morphology: A Long-Term Follow-up Study." Stephane Garrigue, MD, et al.; MD University of Bordeaux, France.

"Impact of Inter-Ventricular Programming to Optimize Severe Heart Failure Patients with Multisite Ventricular Pacing." Pierre Bordachar, MD, et al.; MD University of Bordeaux, France.

"Role of Interventricular Pacing Delay in Patients with Atrial Fibrillation and Cardiac Resynchronisation Therapy." Frank Bracke, MD, et al.; Catharina Hosp., Netherlands.

"Differential Effects of Rights-, Left- and Bi-Ventricular Stimulation in the Rapid Pacing Canine Model of Heart Failure: Evidences for a Direct Mechanical Effect of Different Sites of Stimulation." Bernard Thibault, MD, et al.; Montreal Heart Inst., Montreal, Canada.

"Long Term Results of Cardiac Resynchronization Therapy in Patients with Permanent Atrial Fibrillation." Maurizio Gasparini, MD, et al.; IRCCS, Pavia, Italy.

"Comparison Between Uni-Ventricular Pacing and Biventricular Pacing After AV Nodal Ablation on Systolic Function of Heart Failure Patients with Atrial Fibrillation." Angelo Auricchio, MD, et al.; University Hosp, Germany and Guidant Corp., MN.

Morton M. Mower, U.S. Appl. No. 10/214,474, entitled "Method and Apparatus for Treating Hemodynamic Disfunction," filed Aug. 8, 2002 (Continuation Reissue Application of U.S. Pat. No. 4,928,688).

Picture of Biventricular Pacer manufactured by American Optical Co., American Optical Corp., Research Division, Biventricular Pacer Device, 1975.

Ahn et al., "Disparity Between Left Ventricular and Biventricular Pacing Thresholds," NASPE Abstracts, Pace, vol. 26, Part II, Apr. 2003, Abstract No. 96.

Aranda et al., "A New Pacemaker for Simultaneous Biventricular Stimulation of the Human Heart," Clin. Res., vol. XXIV, No. 3, p. 206A (1976).

Auricchio et al., "Comparison Between Uni-Ventricular Pacing and Biventricular Pacing After AV Nodal Ablation on Systolic Function of Heart Failure Patients with Atrial Fibrillation," NASPE Abstracts, Pace, vol. 26, Part II, Apr. 2003, Abstract No. 613.

Badeer, "Relation of ECG to Mechanical Events," Cardiovascular Physiology, 1984, 6:57-58.

Bailon et al., "Some Data for an Unanswered Question: Choosing the Ventricular Electrode Place." Pacing and Clinical Electrophysiology, vol. 8, No. 3, Part II, p. A-11 (1985).

Bakker et al., "Beneficial Effects of Biventricular Pacing in Congestive Heart Failure," Pace, Apr. 1994, 17 (4):820.

Bakker et al., "Biventricular Pacing in Congestive Heart Failure," Clinical Research, vol. 42, No. 2., Apr. 1994, p. 327A.

Bakker et al., "Biventricular Pacing Improves Functional Capacity in Patients with End-Stage Congestive Heart Failure," Pace, NASPE Abstracts, 1995 (18):825.

Barold et al., "First Reports of Electrical Multisite Ventricular Activation in Humans," Pace, Dec. 2000, (23):2117-2119.

Bashir et al., "Combined Use of Transesophageal Echo and Fluoroscopy for the Placement of Left Ventricular Pacing Leads via the Coronary Sinus," Pace, Oct. 2003, (26):1951-1954.

Befeler et al., "Programmed Simultaneous Biventricular Stimulation in Man, with Special Reference to its Use in the Evaluation of Intraventricular Reentry," Eur. J. of Cardiology, vol. 9, No. 5, pp. 369-378 (1979).

Benchimol et al., "Cardiac Hemodynamics During Stimulation of the Right Atrium, Right Ventricle, and Left Ventricle in Normal and Abnormal Hearts," Circulation, vol. 33, Jun. 1966. pp. 933-944.

Benchimol et al., "Contribution of Atrial Systole to the Cardiac Function at a Fixed and at a Variable Ventricular Rate," The American Journal of Cardiology, vol. 16, No. 1, Jul. 1965, pp. 11-21.

Blackburn et al., "Ventricular Pacing from the Coronary Sinus of a Patient with a Fontan Circulation," Br. Heart J., 1993, (70):578-579.

Bocchiardo et al., "Efficacy of Biventricular Sensing and Treatment of Ventricular Arrhythmias," Pace, vol. 23, Nov. 2000, 1989-1991.

Bordachar et al., "Impact of Inter-Ventricular Programming to Optimize Severe Heart Failure Patients with Multisite Ventricular Pacing," NASPE Abstracts, Pace, vol. 26, Part II, Apr. 2003, Abstract No. 92.

Bourassa, "Hemodynamic Studies During Intermittent Left Bundle Branch Block," American Journal of Cardiology, Dec. 1962, 792-799.

Bove et al., "Ventricular Interdependence," Prog. Cardiovasc. Dis., Mar.-Apr. 1981; 23(5):365-388.

Bracke et al., "Extraction of Pacemaker and Implantable Cardioverter Defibrillator Leads: Patient and Lead Characteristics in Relation to the Requirement of Extraction Tools," Pace, Jul. 2002, (25):1037-1040.

Bracke et al., "Role of Interventricular Pacing Delay in Patients with Atrial Fibrillation and Cardiac Resynchronisation Therapy," NASPE Abstracts, Pace, vol. 26, Part II, Apr. 2003, Abstract No. 621.

Broka et al., "Hemodynamic Effects of Atrio-Biventricular Pacing," Ann. Thoracic Surg., 1995, (60):1156.

Brownlee et al., "New Functional Configurations for Adaptive Pacemakers," 28$^{th}$ ACEMB, New Orleans. Sep. 20-24, 1975, p. 84.

Brownlee et al., "Advances in ventricular synchronous demand cardiac pacemakers," Med. Instrum., Mar.-Apr. 1978; 12(2):94-99.

Brownlee et al., "New Interference Sensing Demand Pacemaker Functions," IEEE Transaction on Biomedical Engineering, May 1978, vol. BME 25, No. 3, pp. 264-269.

Bulava et al., "Triple-Site Pacing in Patients with Biventricular Device, Incidence of the Phenomenon and Cardiac Resynchronization Benefit," NASPE Abstracts, Pace, vol. 26, Part II, Apr. 2003, Abstract No. 617.

Castellanos et al., "Bipolar Coronary Sinus Lead for Left Atrial and Left Ventricular Recording," American Heart Journal, 1971, vol. 81, No. 6, 832-836.

Castellanos et al., "Measurement of Conduction Times With Catheter Electrodes During Pacing From Different Ventricular Sites," British Heart Journal, 1975, (37):242-248.

Castellanos et al., "Unusual QRS Complexes Produced by Pacemaker Stimuli," American Heart Journal, Jun. 1969, vol. 77, No. 6, 732-742.

Cazeau et al., "Four Chamber Pacing in Dilated Cardiomyopathy," Pace, Nov. 1994, Part II, vol. 17, 1974-1979.

Cazeau et al., "Multisite Pacing for End-Stage Heart Failure," Pace, Nov. 1996, (19):1748-1757.

Cazeau et al., "Echocardiographic Modeling of Cardiac Dyssynchorny Before and During Multisite Stimulation: A Prospective Study," Pace, Jan. 2003, Part II, (26):137-143.

Chamorro et al., "Ejection VAVE; EF and Phase Histogram to Evaluate a Correct Programation of AV Delay in DDD Pacemakers," European Journal of Nuclear Medicine, vol. 8, No. 5, pp. A 36 (1983).

Cohen et al., "Hemodynamic Responses to Rapid Pacing: A Model for Tachycardia Differentiation," Pace, Nov. 1988, (11):1522-1528.

Cordis Articor Manual, Implantable P-Wave Synchronized Cardiac Pacers, Model 145, 149-Rev. 3A, Oct. 1973, pp. I-1 to VIII-1.

Curtiss et al., "Electrocardiographically Discrete Right and Left Ventricular QRS Complexes: A Case Report," J. Electrocardiol., Apr. 1987; 20(2):162-168.

D'Aiotolo et al., "Tratamiento De Las Arritmias Cardiacas," Buenos Aires (1968) (in Spanish). pp. 1-112.

David et al., "Atrial Alternans: Experimental Echocardiographic and Hemodynamic Demonstration During Programmed Pacing," Am. J. of Cardiology, Sep. 1981, vol. 48, pp. 468-472.

(56) References Cited

OTHER PUBLICATIONS

Dawson et al., "Regional left ventricular wall motion in pacing induced angina," Br. Heart J., 1988, 59(3):309-318.

Dawson et al., "Left ventricular filling and early diastolic function at rest and during angina in patients with coronary artery disease," Br. Heart J. 1989, 61(3):248-257.

De Teresa et al., "An Even More Physiological Pacing: Changing the Sequence of Ventricular Activation," Cardiac Pacing: Proceedings of the VIIth World Symposium on Cardiac Pacing, Vienna, May 1-5, 1983, Steinkopff Verlag Darmstadt 1983, pp. 395-400.

De Teresa et al., "Haemodynamics of Ventricular Depolarization Sequence During Permanent Cardiac Pacing," Cardio Stimolazione, vol. 2, No. 3, p. 225 (1984).

De Teresa et al., "Haemodynamics of Ventricular Depolarization Sequence During Permanent Cardiac Pacing," Progress in Clinical Pacing, Proceedings Ed. by Santini et al., pp. 888-894, Rome (1984).

Dreifus et al., "Use of atrial and bifocal cardiac pacemakers for treating resistant dysrhythmias," Eur. J. Cardiol., Dec. 1975.; 3(4):257-266.

Dreifus et al., "Effect of multiple simultaneous activation sites (biventricular pacing) on ventricular depolarization and ventricular arrhythmias," Cardiac Pacing, Proceedings of the Vth International Symposium, Tokyo, Mar. 1976, pp. 33-39.

Duck et al., "Vorhofsynchrone Ventrikelstimulation mit verkürzter a.v. Verzögerungszeit als Therapieprinzip der hypertrophischen obstruktiven Kardiomyopathie" "[Atrial Synchronous Ventricular Stimulation With Reduced a.v. Delay Time as a Therapeutic Principle in Hypertrophic Obstructive Cardiomyopathy]," Z. Gesamte Inn. Med., Sep. 15, 1984, (39):18 437-447. (German with English-Language Abstract Attached).

Enjoji et al., "Evaluation of Bi-Atrial Pacing and Single Site Right Atrial Pacing for the Prevention of Atrial Fibrillation," Circ. J., 66(1):70-74 (Jan. 2002), web abstract only from http://www.ncbi.nlm.nih.gov, 1 page.

Erdogan et al., "Proportion of Candidates for Cardiac Resynchronization Therapy," Pace, Jan. 2003, Part II, 26:152-154.

Fei et al., "Effects of Multisite Ventricular Pacing on Cardiac Function in Normal Dogs and Dogs with Heart Failure," Journal of Cardiovascular Electrophysiology, Jul. 1999, 10(7):935-946.

Finney, Jr., "Hemodynamic Alterations in Left Ventricular Function Consequent to Ventricular Pacing," American J. Physiology, 1965, 208(2):275-282.

Foster et al., "Acute Hemodynamic Effects of Atrio-Biventricular Pacing in Humans," Annals of Thoracic Surg., 1995, 55:294-300.

Funke, "[Optimized Sequential Pacing of Atrium and Ventricle—A New Therapeutic Concept in the Treatment of Bradycardial Dysrhythmias]," Herz/Kreisl., Oct. 1978; 10(10):479-483 (German with English-Language Abstract and English Translation Attached).

Furuta et al., "[Assessment of interaction between the left and right ventricles using pressure-volume loops in various heart diseases]," J. Cardiol., Jun. 1988: 18(2):477-491. (Japanese with English Abstract and Figure Captions).

Garrigue et al., "Intra-Left Ventricular Mechanical Asynchrony is an Independent Predictive Factor of Heart Failure Worsening Regardless of the QRS Width and Morphology: A Long-Term Follow-Up Study," NASPE Abstracts, Pace, vol. 26, Part II, Apr. 2003, Abstract No. 150.

Gasparini et al., "Long Term Results of Cardiac Resynchronization Therapy in Patients with Permanent Atrial Fibrillation," NASPE Abstracts, Pace, vol. 26, Part II, Apr. 2003, Abstract No. 700.

Gasparini et al., on behalf of the Italian InSync ICD Registry Investigators, "Cardiac Resynchronization and Implantable Cardioverter Defibrillator Therapy: Preliminary Results from the InSync Implantable Cardioverter Defibrillator Italian Registry," Pace, Jan. 2003, 26(1):2, 148-151.

Gasparini et al., "Beneficial Effects of Biventricular Pacing in Patients with a 'Narrow' QRS," Pace, Jan. 2003, 26(1):2, 169-174.

Gibson et al., "Effect of Changes in Ventricular Activation on Cardiac Haemodynamics in Man: Comparison of Right Ventricular, Left Ventricular, and Simultaneous Pacing of Both Ventricles," Br. Heart J., May 1971; 33(3):397-400.

Gilmore et al., "Synchronicity of Ventricular Contraction: Observations Comparing Haemodynamic Effects of Atrial and Ventricular Pacing," Br. Heart J., May 1963; 25:299-307.

Greatbatch, "The Making of the Pacemaker: Celebrating Lifesaving Invention," Prometheus Books, 2000. pp. 1-260, particularly pp. 14-19.

Gomez-Doblas et al., "Ventricular Geometry and Heart Failure," Rev. Esp. Cardiol., Jan. 1999, 52(1):47-52. Review. (Spanish with English Abstract).

Grover et al., "Endocardial Pacing Site Affects Left Ventricular End-Diastolic Volume and Performance in the Intact Anesthetized Dog," Circulation Research, Jul. 1983, 53(1):72-85.

Haas et al., "Pacemaker-Induced Cardiovascular Failure," Am. J. of Cardiology, vol. 33, pp. 295-299 (Feb. 1974).

Hauser et al., "Performance of Pacemaker and Implantable Cardioverter Defibrillator Pulse Generators and Leads: Results from the Multicenter Registry," The XIIth World Congress on Cardiac Pacing & Electrophysiology, Hong Kong, Feb. 19-22, 2003, pp. 173-179.

Hayes et al., "Cardiac Pacing: How it Started, Where We Are, Where We Are Going," Pace, May 2004, 27:693-704.

Hochleitner et al., "Usefulness of Physiologic Dual-chamber Pacing in Drug-Resistant Idiopathic Dilated Cardiomyopathy," American Journal of Cardiology, Jul. 15, 1990, (66):198-202.

Hughes et al., "Effect of Stimulation Site on Ventricular Threshold in Dogs with Heart Block," American Heart Journal, Jan. 1975, 89(1):68-73.

Hughes et al., "Two to Three Years of Failure-Free Testing of a Rechargeable Pacemaker in Experimental Complete Heart Block," Circulation, Aug. 1976, 54(2):263-266.

Hughes et al., "The Effects of Electrode Position on the Detection of the Transvenous Cardiac Electrogram," Pace, 1980, 3(6):651-655.

Hunt et al., "Long-term Electrode Catheter Pacing from Coronary Sinus," Medical Memoranda, British Medical Journal, Nov. 23, 1968, pp. 495-496.

Janosik et al., "The Hemodynamic Benefit of Differential Atrioventricular Delay Intervals for Sensed and Paced Atrial Events During Physiologic Pacing," J. Am. Coll. Cardiol., Aug. 1989, 14(2):499-507.

Jeffrey, Excerpts from *Machines in Our Hearts*, 2001, The John Hopkins University Press, Chapter 2, pp. 36-39, 65-66, 90-100, 118-120, 170-171, and 236-237.

Jimenez-Navarro et al., Correspondence to the Editor about "Left Ventricular Assist Device," N. Engl. J. Med., Mar. 28, 2002, 346(13):1023-1025; author reply 1023-1025.

Karlöf, Ingvar, "Haemodynamic Effect of Atrial Triggered Versus Fixed Rate Pacing at Rest and During Exercise in Complete Heart Block," Acta. Med. Scand., 197(3):195-206, Mar. 1975.

Kawamura et al., "[83. Experimental Study of RV-LV Simultaneous Pacing as More Physiological Pacing]," Idem Job No. 0412-137, 1982, pp. 285-286. (Japanese with English Translation).

Kennergren et al., "Cardiac Lead Extraction with a Novel Locking Stylet," Journal of Interventional Cardiac Electrophysiology, 2000, V.4, pp. 591-593.

Kerr et al., "Transvenous Atrial Pacing Following Amputation of the Atrial Appendage at Open Heart Surgery," Pace. Jul.-Aug. 1985, (8):497-501.

Kerr et al., "Atrial Pacing: Efficacy and Safety," Pace, Jul. 1989, 12(1):1049-1054.

Klug et al., "Pacemaker Lead Extraction With the Needle's Eye Snare for Countertraction via a Femoral Approach," Pace, Jul. 2002, 25(7):1023-1028.

Lane et al., "Multisite Right Ventricular Pacing: An Alternative Form of Cardiac Resynchronisation," NASPE Abstracts, Pace. vol. 26, Part II, Apr. 2003, Abstract No. 190.

Lane et al., "The Influence of Lead Position and Interventricular Pacing Interval for Optimal Cardiac Resynchronisation Therapy," NASPE Abstracts, Pace, vol. 26, Part II, Apr. 2003, Abstract No. 701.

Lattuca et al., "Bi-Ventricular Pacing to Improve Cardiac Hemodynamics," Clinical Research, Oct. 1990, 38 (3):882A.

(56) References Cited

OTHER PUBLICATIONS

Lemery, "Bi-Atrial Mapping of Atrial Arrhythmias," Card. Electrophysiol. Rev., 6(4):378-382 (Dec. 2002), web abstract only from http://www.ncbi.nlm.nih.gov, 1 page.

Lima et al., "Incomplete Filling and Incoordinate Contraction as Mechanisms of Hypotension during Ventricular Tachycardia in Man," Circulation, vol. 68, No. 5, pp. 928-937 (1983).

Lister et al., Effect of Pacemaker Site on Cardiac Output and Ventricular Activation in Dogs with Complete Heart Block,: Am. J. of Cardiology, vol. 14, pp. 494, 496, 500 (1964).

Magder et al., "Effect of Negative Pleural Pressure on Left Ventricular Hemodynamics," Am. J. of Cardiology, Sep. 1, 1983, 52(5), pp. 588-593 (Abstract Only).

Mann et al., "Importance of Pacing Site in Entrainment of Ventricular Tachycardia," J. Am. College of Cardiology, vol. 5, No. 3, pp. 781-787 (1985).

Marchlinski et al., "Atrial and Ventricular Burst Pacing from a Coronary Sinus Catheter: Relation to Position of Radiofrequency Transmitter," Pace, May-Jun. 1985, 8(I), 399-401.

McIntosh et al., "The Hemodynamic Consequences of Arrhythmias," Prog. Cardiovasc. Dis., 8(4):330-363 (1966).

Medtech Insight, "Hot Topics in Heart Failure," Jun./Jul. 2004, cover page and pp. 190-200.

Mehta et al., "Cardiology's 10 Greatest Discoveries of the 20th Century," Texas Heart Institute Journal, 2002, 9(3):164-171.

Mercando et al., "Measurement of Differences in Timing and Sequence Between Two Ventricular Electrodes as a Means of Tachycardia Differentiation," Pace, Nov.-Dec. 1986, 9(II):1069-1078.

Mirowski et al., "A Chronically Implanted System for Automatic Defibrillation in Active Conscious Dogs," Circulation, Jul. 1978; 58(1):90-94.

Mirowski et al., "Clinical Experience with the Implantable Cardioverter-Defibrillator," Annals of the New York Academy of Sciences, 1984, 427:297-306.

Mirowski et al., "Clinical experience with the automatic implantable defibrillator," Arch. M. Com., 1985, pp. 39-42.

Mirowski et al., "The Automatic Implantable Cardioverter-Defibrillator," Pace, May-Jun. 1984, Part II, 7:534-540.

Mirowski et al., "Use of the automatic implantable cardioverter-defibrillator in the treatment of malignant ventricular tachyarrhythmias," Herz, 1984, 9(2):83-89.

Mirowski et al., "Clinical Performance of the Implantable Cardioverter-Defibrillator," Pace, Nov.-Dec. 1984, Part II, 7:1345-1350.

Molhoek et al., "QRS Duration and Shortening to Predict Clinical Response to Cardiac Resynchronization Therapy in Patients with End-Stage Heart Failure," Pace, Mar. 2004, 27:308-313.

Moore et al., "Electrophysiological Studies on Pacing Techniques to Prevent Ventricular Fibrillation," Chapter 22 from Nonpharmacological Therapy of Tachyarrhythmias, Futura Pub. Co., 1987, pp. 345-358.

Mortensen et al., "Sequential Biventricular Pacing: Evaluation of Safety and Efficacy," Pace, Mar. 2004, 27:339-345.

Moss, "Long-Term Pervenous Atrial Pacing From the Proximal Portion of the Coronary Vein," JAMA, Jul. 28, 1969, 209(4):543-545.

Moulopoulos et al., "Effect of Site and Intensity of Pacing on Left Ventricular Performance," J. Electocardiology, 16(4):409-415 (1983).

Mower et al., "Unusual Patterns of Conduction Produced by Pacemaker Stimuli," Am. Heart J., Jul. 1967; 74(1):24-28.

Mower et al., "Automatic Implantable Cardioverter-Defibrillator Structural Characteristics," Pace, Nov.-Dec. 1984, 7(No. 6, Pt 2):1331-1337.

Navarro-Lopez et al., "Guideline 8. Criteria for Hospitalization," Rev. Esp. Cardiol., 1997, 50(Supp. 1):47-48. (Spanish with English abstract).

Navarro-Lopez et al., "Guideline 1. Diagnosis of Heart Failure and Ventricular Dysfunction," Rev. Esp. Cardiol., 1997, 50(Supp. 1):3-8 (Spanish with English abstract).

Navarro-Lopez et al., "Guideline 4. Management of Congestive Heart Failure," Rev. Esp. Cardiol., 1997, 50(Supp. 1):27-31. (Spanish with English abstract).

Navarro-Lopez et al., "Guidelines for the Diagnosis and Management of Heart Failure and Cardiogenic Shock," Rev. Esp. Cardiol., 1999, 52(Supp. 2):1-54. (Spanish with English abstract).

Ong et al., "Cephalic vein guide wire technique for implantation of permanent pacemakers," American Heart Journal, Oct. 1987, 4(1):753-756.

Park et al., "Effect of Alteration of Left Ventricular Activation Sequence on the Left Ventricular End-Systolic Pressure-Volume Relation in Closed-Chest Dogs," Circulation Research, vol. 57, No. 5, Nov. 1985, pp. 706-717.

Patel et al., Letters to the Editor. "Coronary Sinus Pacing," Circulation, vol. 58, No. 1, Jul. 1978, pp. 187-189.

Peschar et al., "Left Ventricular Septal and Apex Pacing for Optimal Pump Function in Canine Hearts," Journal of the American College of Cardiology, 2003, 41(7):1218-1226.

Platia et al., "Management of the Prolonged QT Syndrome and Recurrent Ventricular Fibrillation with an Implantable Automatic Cardioverter-Defibrillator," Clinical Cardiology, 1985, 8:490-493.

Platia et al. "Sensitivity of various extrastimuls techniques in patients with serious ventricular arrhythmias," American Heart Journal, Oct. 1983, 106(4):698-703.

Platia et al., "Treatment of Malignant Ventricular Arrhythmias With Endocardial Resection and Implantation of the Automatic Cardioverter-Defibrillator," The New England Journal of Medicine, Jan. 1986, 314(4):213-216.

Prinzen et al., "Relation Between the Pacing Induced Sequence of Activation and Left Ventricular Pump Function in Animals," Pace, Apr. 2002, Part I, 25(4):484-498.

Reid et al., "Implantable Cardioverter-Defibrillator: Patient Selection and Implantation Protocol," Pace, Nov.-Dec. 1984, Part II, 7:1338-1344.

Reid et al., "Clinical Evaluation of the Internal Automatic Cardioverter-Defibrillator in Survivors of Sudden Cardiac Death," Am. J. Cardiol., Jun. 1983;51:1608-1609.

Ritter, "Editorial," Pace, Jan. 2003, Part II, 26:136.

Rogel et al., "The Universal Pacer: A synchronized-demand pacemaker," J. Thorac. Cardiovasc. Surg., Mar. 1971; 61(3):466-471.

Rosenheck et al., "Noninstrumental Pacemaker and Defibrillator Lead Removal: The Importance of the Rotation Forces," Pace, vol. 25, No. 7 Jul. 2002, pp. 1029-1036.

Rosenqvist et al., "Relative Importance of Activation Sequence Compared to Atrioventricular Synchrony in Left Ventricular Function," Am. J. of Cardiology, vol. 67, Jan. 15, 1991, pp. 148-156.

Samet et al., "Electrical Activation and Mechanical Asynchronism in the Cardiac Cycle of the Dog," Circulation Research, vol. VII, Mar. 1959, pp. 228-233.

Santamore et al., "A Theoretical and Experimental Model of Ventricular Interdependence," Basic Res. Cardiol., Sep.-Oct. 1986; 81(5):529-538.

Schlant et al., "Modification of the Law of the Heart: Influence of Early Contracting Areas (P)," Supp. to Circulation, vols. XXIX and XXX, Oct. 1964, pp. 153-154.

Shefer et al., "Left Ventricular Function During Physiological Cardiac Pacing: Relation to Rate, Pacing Mode, and Underlying Myocardial Disease," Pace, vol. 10, Mar.-Apr. 1987, pp. 315-325.

Silva et al., "Biventricular Stimulation: A More Physiologic Pacing," 4th European Symposium on Cardiac Pacing, May 28-31, 1989, Abstract 339, pp. 148.

Silva, "Influencia de la Localizacion de la Estimulacion Electrica Ventricular Sobre la Eficiencia Cardiaca. Estudio Experimental Y Clinico," Tesis Doctoral para la Universidad Autonoma De Madrid Facultad de Medicina (1987), pp. 1-150 (Doctoral Thesis, in Spanish).

Silva et al., "Biventricular Stimulation: An Approach to Physiologic Cardiac Stimulation," International Congress of Cardiology, Abstracts, pp. 132 (Nov. 1988).

Sodi-Pollares et al., "General Considerations About the Activation Process of the Heart," Deductive and Polyparametric Electrocardiography, 1970, pp. 30-41.

(56)　　　　　References Cited

OTHER PUBLICATIONS

Takeshita et al., "Effect of Intermittent Left Bundle Branch Block on Left Ventricular Performance," Am. J. of Medicine, vol. 56, Feb. 1974, pp. 251-255.

Tedrow et al., "Feasibility of Adjusting Cardiac Resynchronization by Manipulating Left Ventricular Pacing Stimulus Strength," NASPE Abstracts, Pace, vol. 26, Part II, Apr. 2003, Abstract No. 15.

Thibault et al., "Differential Effects of Right-, Left- and Bi-Ventricular Stimulation in the Rapid Pacing Canine Model of Heart Failure: Evidences for a Direct Mechanical Effect of Different Sites of Stimulation," NASPE Abstracts, Pace, vol. 26, Part II, Apr. 2003, Abstract No. 430.

Tsagaris et al., "Species Variablility in Hemodynamic Response to Paired-Pulse Stimulation," Am. J. of Physiology, Jun. 1969. 216(6):1409-1417.

Tyers, "Comparison of the Effect on Cardiac Function of Single-Site and Simultaneous Multiple-Site Ventricular Stimulation After A-V Block," J. Thoracic and Cardiovas. Sur., vol. 59, No. 2, pp. 211-217 (1970).

Tyers et al., "A New Device for Nonoperative Repair of Internal Cardiac Pacemakers," Archives of Surgery, Jun. 1966, vol. 92:901-904.

Tyers, "Maximum Cardiac Performance After Complete Heart Block," Surgical Forum, vol. XVIII, American College of Surgeons, 1967, pp. 132-133.

Tyers, "Optimal electrode implantation site for asynchronous dipolar cardiac pacing," Annals of Surgery, Feb. 1968, 167(2):168-179.

Tyers et al., "An Integrated Program for Safe Permanent Internal Cardiac Pacing," The Journal of Cardiovascular Surgery, 11th World Congress of International Cardiovascular Society, Barcelona, Sep. 27-29, 1973, Special issue, pp. 163-166.

Tyers et al., "Effect of Site of Synchronous Unipolar Ventricular Stimulation and Volume Loading on Cardiac Function," J. Surg. Res., Oct. 1973; 15(4):271-284.

Tyers et al., "Comparative studies of 'state of the art' and presently used clinical cardiac pacemaker electrodes," Journal of Thoracic and Cardiovascular Surgery, St. Louis, vol. 67, No. 6, Jun. 1974, pp. 849-856.

Tyers et al., "The Advantages of Transthoracic Placement of Permanent Cardiac Pacemaker Electrodes," Journal of Thoracic and Cardiovascular Surgery, Jan. 1975, 69(1):8-14.

Tyers et al., "The unfulfilled promise of demand pacing," Journal of Thoracic and Cardiovascular Surgery, Nov. 1976, 72(5):813-814.

Tyers et al., "Improved R-wave Detection with Intramyocardial Electrodes," 30th ACEMB, Los Angeles Hilton, Los Angeles, CA, Nov. 5-9, 1977, p. 268.

Tyers et al., "R-Wave Detection for Demand Pacing—The Superiority of Intramyocardial Over Endocardial Electrodes," J. Surg. Res., Apr. 1978, 24(4):316-320.

Tyers et al., "Myocardial Stimulation Impedance: The Effects of Electrode, Physiological, and Stimulus Variables," Annals of Thoracic Surgery, 27(1):63-69 (1979).

Tyers et al., "Multiprogrammable Pacemakers," Canadian Journal of Surgery, 1981, 24(3):252-256.

Tyers et al., "Current Status and Future of Programmable Pacing," Vogel, J.H.K. (Ed.). Cardiovascular Medicine, vol. 1., Raven Press: New York, N.Y., (1982), pp. 355-362.

Tyers et al., "Current Status of Sensor-Modulated Rate-Adaptive Cardiac Pacing," Journal of the American College of Cardiology, 1990 15(2):412-418.

Tyers et al., "Medical Device Review in Canada," Pace, Mar. 1995, 18(3):472-473.

Tyers et al., "Coradial Bipolar Lead Implant and Follow-Up Experience," poster presentation at the North American Society for Pacing and Electrophysiology (NASPE), 17th Annual Scientific Sessions. Seattle, WA, May 15-18, 1996, 4 pages.

Tyers et al., "Removal of Permanent Endocardial Pacing Leads (1981-1997)," Heartweb, vol. 4, No. 4, Feb. 1999, (Article No. 9920003), pp. 1-8.

Tyers et al., "Bipolar leads for use with permanently implantable cardiac pacing systems: A review of limitations of traditional and coaxial configurations and the development and testing of new conductor, insulation, and electrode designs," J. Invest. Surg., 1997, 10(1):1-15.

Tyers et al., "Similar indications but different methods: Should there be a consensus on optimal lead extraction techniques?", Pace, Jul. 2002, 25(7):1019-1022.

Tyers et al., "Bifocal/Biatrial Pacing in Clinical Practice," The XIIth World Congress on Cardiac Pacing & Electrophysiology, Hong Kong, Feb. 19-22, 2003, pp. 715-717.

Tyers et al., "Coronary sinus lead extraction," The XIIth World Congress on Cardiac Pacing & Electrophysiology, Hong Kong, Feb. 19-22, 2003, pp. 741-743.

Tyers et al., "Surgical Complications of Pacemaker Implant," The XIIth World Congress on Cardiac Pacing & Electrophysiology, Hong Kong, Feb. 19-22, 2003, pp. 745-760.

Val-Mejias et al., "Paced QRS Width Narrows with Increasing Pacing Voltages: Implications for Ventricular Resynchronization," NASPE Abstracts, Pace, vol. 26, Part II, Apr. 2003, Abstract No. 702.

Van Gelder et al., "The Influence of Intrinsic Conduction on Left Ventricular dP/dt During Biventricular Pacing in Cardiac Resynchronisation Therapy," NASPE Abstracts, Pace, vol. 26, Part II, Apr. 2003, Abstract No. 94.

Waldo et al., "Ventricular Paired Pacing to Control Rapid Ventricular Heart Rate Following Open Heart Surgery," Circulation, Jan. 1976, 53(1):176-181.

Walsh et al., "Differentiation of Sinus Rhythms for Supraventricular Tachydysrhythmias by Activation Sequence and Timing," Pace Dec. 1990;13(12 Pt 2): 1972-9 (Abstract Only).

Watkins, Jr. et al., "Surgical Techniques for Implanting the Automatic Implantable Defibrillator," Pace, Nov.-Dec. 1984, Part II, 7:1357-1362.

Watkins et al., "The Treatment of Malignant Ventricular Arrhythmias with Combined Endocardial Resection and Implantation of the Automatic Defibrillator: Preliminary Report," The Annals of Thoracic Surgery, Jan. 1984, 37(1):60-64.

Watkins et al., "Malignant Ventricular Arrhythmias," The Annals of Thoracic Surgery, Jan. 1984, 37(1):65-66.

Watkins et al., "Automatic Implantable Defibrillator," The Journal of Thoracic and Cardiovascular Surgery, Sep. 1983, 86(3):382-387.

Watkins et al., "Automatic Defibrillation in Man: Is It Feasible?" The American Journal of Surgery, Jun. 1983, 145:752-755.

Waxman et al., "Ventricular Pacing from the Middle Cardiac Vein Mimicking Supraventricular Morphology" Pace, vol. 2, Mar.-Apr. 1979, pp. 203-207.

William-Olsson et al., "The Effect of Pacemaker Electrode Site on Cardiac Output," J. Thoracic and Cardiovas. Surg., vol. 45, No. 5, pp. 618-621 (1963).

Wish et al., "Optimal Left Atrioventricular Sequence in Dual Chamber Pacing-Limitations of Programmed A-V Interval," JACC, vol. 3, No. 7, Feb. 1984, p. 507 (Abstract).

Witte et al., "Transvenous Atrial Synchronized Pacing," Advances in Pacemaker Technology, Springer-Verlag Pub., 1975, pp. 99-120.

Yoshimori, "An Experimental Study on the Site for Ventricular Pacing of a Dog Heart with Special Reference to Biventricular Pacing," Nippon Ika Daigaku Zasshi, vol. 54, No. 3 (1987), pp. 267-276. (Japanese with English-Language Abstract and English Translation Attached).

Zile et al., "Right Ventricular Pacing Reduces the Rate of Left Ventricular Relaxation and Filling," J. Am. Coll. Cardiol., vol. 10, No. 3, pp. 702-709 (1987).

Zipes et al., "Electrophysiologic Studies on Ventricular Fibrillation," Cardiac Electrophysiology and Arrhythmias, Gruni and Stratton, Pub., 1985, pp. 317-320.

Diotallevi et al., "Rescuing Failed Biventricular Implants Using Right Ventricular Bifocal Pacing to Assure Cardiac Resynchronization Benefits to Heart Failure Patients," Heart Rhythm, vol. 3, No. 5, May Supplement 2006, Abstract No. AB48-2.

(56) References Cited

OTHER PUBLICATIONS

Leclercq et al., "Triple Site Ventricular Pacing for Optimizing Ventricular Resynchronization: Design of the Trip-HF Study; Technical Feasibility," Heart Rhythm, vol. 3. No. 5, May Supplement 2006. Abstract No. AB48-3.

Niazi et al., "Dual-Site Left Ventricular Stimulation Provides Better Resynchronization Response than Conventional Biventricular Stimulation," Heart Rhythm, vol. 3, No. 5, May Supplement 2006, Abstract No. AB42-6.

Yoshida et al., "Tripolar-Ventricular Pacing Improves Both Systolic and Diastolic Left Ventricular Function in Patients with End-Stage Heart Failure," Heart Rhythm, vol. 3, No. 5, May Supplement 2006, Abstract No. P6-96.

Abraham, WT, et al., "Cardiac Resynchronization in Chronic Heart Failure," N. Engl. J. Med., vol. 346, No. 24, 2002, pp. 1845-1853.

Anagnostopoulos, CE, et al., "Transvenous Coronary Sinus Pacemaker: A New Primary Approach to Heart Block in Patients with Tricuspid Prostheses," The Annals of Thoracic Surgery, vol. 9, No. 3, Mar. 1970, pp. 248-252.

Aurrichio A, et al, "Effect of Pacing Chamber and Atrioventricular Delay on Acute Systolic Function of Paced Patients With Congestive Heart Failure," Circulation, vol. 99, No. 23, Jun. 1999, pp. 2993-3001.

Aurrichio A, et al., "Long-Term Clinical Effect of Hemodynamically Optimized Cardiac Resynchronization Therapy in Patients With Heart Failure and Ventricular Conduction Delay," J. Am. Coll. Cardiol., vol. 39, No. 12, 2002, pp. 2026-2033.

Befeler, B, et al., "Cardiovascular Dynamics During Coronary Sinus, Right Atrial, and Right Ventricular Pacing," Am. Heart J.. vol. 81, No. 3, Mar. 1971, pp. 372-380.

Benditt, DG et al., "Sensor-Triggered Rate-Variable Cardiac Pacing: Current Technologies and Clinical Implications," Annals of Internal Med., vol. 107, No. 5, Nov. 1987, pp. 714-724.

Berkovits, B, et al., "Bifocal Demand Pacing," Singapore Med. J., vol. 14, No. 3, Sep. 1973, pp. 316-319.

Berkovits, B. "Demand Pacing," Annals of New York Academy of Sciences, vol. 167, Art. 2, Oct. 1969, pp. 891-895.

Berkovits, B, et al., "Future Generation Pacemakers," Pacemaker Therapy, L. Dreifus ed., 1983, pp. 265-276.

Blanc JJ, et al., "Recurrent Supraventricular Tachycardia: The Efficacy of a Radio Frequency System Inserted into the Coronary Sinus," Archives des Maladies du Coeur et des Vaisseaux, 1978, 71:687-90. (English-language summary on p. 690.).

Blanc JJ, et al., "Evaluation of Different Ventricular Pacing Sites in Patients With Severe Heart Failure: Results of an Acute Hemodynamic Study," Circulation, vol. 96, No. 10, Nov. 1997, pp. 3273-3277.

Blanc JJ, et al., "A Method for Permanent Transvenous Left Ventricular Pacing," Pace, vol. 21, Nov. 1998, pp. 2021-2024.

Bognolo, DA, "Recent Advances in Permanent Pacemaker Implantation Techniques," Modern Cardiac Pacing, Barold SS, ed., Futura Publishing Co., 1985, pp. 199-229.

Bristow MR, et al., "Cardiac-Resynchronization Therapy With or Without an Implantable Defibrillator in Advanced Chronic Heart Failure," N. Engl. J. Med., vol. 350, 2004, 2140-50.

Burkoff. D. et al., "Influence of Pacing Site on Canine Left Ventricular Contraction." Am. J. Physiol. (Heart Circ. Physiol.), 1986:20:H428-H435.

Castellanos, A, et al., "Atrial Demand and AV Sequential Pacemakers," Pacemaker Therapy, L. Dreifus, ed., 1983, pp. 149-164.

Castellanos, A, et al., "Cardiac Pacemakers," Cardiac Surgery 2, vol. 3, No. 2, D. Harken, ed., 1971, pp. 32-44.

Castellanos, A, et al., "Effects of Pacemaker Impulses on Latent Arrhythmias Produced by Intramyocardial Chemical Stimulation," Cardiologia, vol. 51, No. 6, 1967, pp. 340-348.

Castellanos, A, et al., "An Electrical Digitalis Tolerance Test," Am. J. of Medical Sciences, Nov. 1967, pp. 159-168.

Castellanos, A, et al., "The Electrocardiogram and Vectorcardiogram of Ectopic Ventricular Beats," Acta Cardiologica, vol. 28, No. 6, 1973, pp. 562-575.

Castellanos, A, et al., "Electronic Pacemaker Models of Parasystole: With Special Reference to Artificial Intermittent Parasystole With Phase 3 and Phase 4 Protection and to Parasystolic Modulation," Pace, vol. 5, No. 4, Jul. 1982, pp. 537-545.

Castellanos, A, et al., "Evaluacion Clinica De Los Marcapasos Implantados," Boletin de la Associacion Medica de Puerto Rico, vol. 73, No. 12, Dec. 1981, pp. 644-653.

Castellanos, A, et al., "His Bundle Recordings in Atrioventricular Nodal Alternating Wenckebach Periods Ending in 5:1 Atrioventricular Block Coexisting with Paroxysmal Atrioventricular Nodal Block," Chest. vol. 74, No. 3, Sep. 1978, pp. 274-279.

Castellanos, A, et al., "Implantable Demand Pacemaker," Brit. Heart J., vol. 30, 1968, pp. 29-33.

Castellanos, A, et al., "Implantable Pacemakers for Cardiac Tachyarrhythmias." Cardiac Arrythmias: Mechanisms and Management, A. Castellanos, ed., 1980, pp. 159-173.

Castellanos, A, et al., "A New Instrument for Automatic Monitoring and Tape Recording in Infants and Children," Boletin de la Associacion Medica de Puerto Rico, vol. 58, No. 7, Jul. 1966, pp. 355-359.

Castellanos, A., et al., "Pacemaker-Induced Cardiac Rhythm Disturbances," Annals of New York Academy of Sciences, vol. 167, No. 2, Oct. 1969, pp. 903-910.

Castellanos, A, et al., "Pacemaker Vectorcardiography," Am. Heart J., vol. 75, No. 1, Jan. 1968, pp. 6-18.

Castellanos, A, et al., "Pacing in Acute Myocardial Infarction: A Programmed Introduction," Chest, vol. 58, No. 2, Aug. 1970, pp. 152-163.

Castellanos, A, et al., "Preliminary Studies With an Implantable Multimodal A-V Pacemaker for Reciprocating Atrioventricular Tachycardias," Pace, vol. 3, No. 3, May 1980, pp. 257-265.

Castellanos, A, et al., "Repetitive Firing Occurring During Synchronized Electrical Stimulation of the Heart," J. of Thoracic Cardiovascular Surgery, vol. 51, No. 3, Mar. 1966, pp. 334-340.

Castellanos, A, et al., "Sextapolar Catheter Electrode for Temporary Sequential Atrioventricular Pacing," Cardiovascular Research, vol. 8, No. 5, Sep. 1974, pp. 712-714.

Castellanos, A, et al., "Significance of Multiple Responses Produced by Electrical Depolarization of the Heart," Acta Cardiologica, vol. 21, No. 2, 1966, pp. 157-166.

Castellanos, A., et al., "Simultaneous Biventricular Stimulation for Ventricular Arrhythmias," Am. J. Cardiol., vol. 88, Nov. 15, 2001, pp. 1217-1218.

Castellanos, A, et al., "A Study of Arrival of Excitation at Selected Ventricular Sites during Human Bundle Branch Block Using Close Bipolar Catheter Electrodes," Chest, vol. 63 No. 2, Feb. 1973, pp. 208-213.

Castellanos, A, et al., "St-qR Pattern: New Sign for Diagnosis of Anterior Myocardial Infarction During Right Ventricular Pacing," Br. Heart J., vol. 35, Oct. 1973, pp. 1161-1165.

Castellanos, A, et al., "The Use of the Demand Pacemaker in Auriculo-Ventricular Conduction Disturbances," J. of Cardiovascular Surgery, vol. 7, No. 2, Mar.-Apr. 1966, pp. 92-96.

Castellanos, A, et al., "Ventricular-triggered Pacemaker Arrhythmias," Brit. Heart J., vol. 31, 1969, pp. 546-552.

Castellanos, A, et al., "The Wedensky Effect in the Human Heart," Brit. Heart J., vol. 28, 1966, pp. 276-283.

Castillo, C, et al., "Bifocal Demand Pacing," Chest, vol. 59, No. 4, Apr. 1971, pp. 360-364.

Cazeau S, et al., "Effects of Multisite Biventricular Pacing in Patients With Heart Failure and Intraventricular Conduction Delay," N. Engl. J. Med., vol. 344, 2001, pp. 873-880.

Chamorro, JL, et. al., "Quantification of Experimental Myocardial Infarction with 99TcGlucogeptonate," European Journal of Nuclear Medicine, vol. 8, No. 5, 1983, Abstract P104.

D'aiutolo, R, and Posse, R, Tratamiento de Las Arritmias Cardiacas, Buenos Aires 1968 and English-language translation of Chapter 10. De Teresa, E., Grandes Temas de la Medicina: Marcapasos, Nueva Lente, Madrid 1987.

Dreifus, L, et al., "Effects of AV Sequential Versus Asynchronous AV Pacing on Pulmonary Hemodynamics," Pace, vol. 9, No. 2, Mar.-Apr. 1986, pp. 171-177.

Ellenbogen KA, et al., Clinical Cardiac Pacing and Defibrillation, 2nd Edition, Philadelphia, W.B. Saunders Co., 2000.

(56)                    References Cited

OTHER PUBLICATIONS

Elmqvist, R, et al., "An Implantable Pacemaker for the Heart," Medical Electronics: Proceedings of the Second International Conference on Medical Electronics, Smyth, CN, ed., Jun. 1959, London, UK, Iliffe & Sons; pp. 253-254.

Escher, DJW, "Historical Aspects of Cardiac Pacing," Cardiac Pacing (2nd Ed.), Samet, P, et al., eds., New York, Grune & Stratton, 1979, pp. 631-643.

Etienne, Y, et al., "Evaluation of Left Ventricular Based Pacing in Patients With Congestive Heart Failure and Atrial Fibrillation," Am. J. Cardiol., vol. 83, 1999, pp. 1138-1140.

Fields, J, et al., "Surgical Experience With Temporary and Permanent A-V Sequential Demand Pacing," J. of Thoracic and Cardiovascular Surgery, vol. 66, No. 6, Dec. 1973, pp. 865-877.

Fletcher, FW, et al., "Effect of Pacemaker Location on Cardiac Function in Complete Heart Block," Am. J. Physiol., 1963; 205:1232-34.

Gabrielle, O. F., "Pacing via Coronary Sinus," N. Engl. J. Med., vol. 280, No. 4, 1969, p. 219.

Greenberg, et al., "Coronary Sinus Pacing: Clinical Follow-up," Circulation, vol. 57, No. 1, Jan. 1978, pp. 98-103.

Hayes, D., "Pacemakers" in Comprehensive Cardiovascular Medicine, EJ Topol, ed., Philadelphia, Lippincott-Raven Publishers, 1998, pp. 2099-2132.

Higgins SL, et al. "Cardiac Resynchronization Therapy for the Treatment of Heart Failure in patients With Intraventricular Conduction Delay and Malignant Ventricular Tachyarrhythmias," J. Am. Coll. Cardiol., Vo. 42, No. 8, 2003, pp. 1454-1459.

Holmes, DR, et al., "Pacemaker Implantation Techniques," in Electrical Therapy for Cardiac Arrhythmias, Saksena, S, et al., eds., Philadelphia, WB Saunders Co., 1990, pp. 173-190.

Kass DA, et al., "Improved Left Ventricular mechanics From Acute VDD Pacing in Patients With Dilated Cardiomyopathy and Ventricular Conduction Delay," Circulation, vol. 99, No. 12, Mar. 1999, pp. 1567-1573.

Kastor, J, et al., "Variations in Discharge Rate of Demand Pacemakers Not Due to Malfunction," Am. J. of Cardiology, vol. 25, No. 3, Mar. 1970, pp. 344-348.

Keller, J. Walter, "Atrial and Ventricular Syncrhony: The Engineering-Physiology Interface," Annals of the New York Academy of Sciences, vol. 167, 1969, pp. 869-885.

Kramer, D. H et al., "Permanent Pervenous Atrial Pacing from the Coronary Vein," Circulation, vol. 42, 1970, pp. 427-436.

Leclercq C, et al., "Acute Hemodynamic Effects of Biventricular DDD Pacing in Patients With End-Stage Heart Failure," J. Am. Coll. Cardiol., vol. 32, No. 7, Dec. 1998, pp. 1825-1831.

Lemberg, L, et al., "Demand and Bifocal Demand Pacing," Singapore Med. J., vol. 14, No. 3, Sep. 1973, pp. 222.

Lemberg, L, et al., "Pacemaking on Demand in AV Block," JAMA, vol. 191, No. 1, Jan. 1965, pp. 106-108.

Lemberg, L, et al., "Systolic and Diastolic Pacemaker Induced Repetitive Firing in the Human Heart: Analysis of 23 Cases," J. Electrocardiology, vol. 2 No. 4, Oct. 1969, pp. 353-362.

Lown, B, et al., "Comparison of Alternating Current with Direct Current Electroshock Across the Closed Chest," Am. J. of Cardiology, Aug. 1962, pp. 223-233.

Lurie KL, et al., "Development of Multifunctional Coronary Sinus Catheter," RBM (Revue Europeenne De Technologie Biomedicale) 1994, 16:159-61.

Mansouratii J, et al., "Left Ventricular-based Pacing in Patients With Chronic Heart Failure: Comparison of Acute Hemodynamic Benefits According to Underlying Heart Disease," European Journal of Heart Failure, 2 (2000):195-99.

Maytin, O, et al., "Diagramatic Representation of Pacemaker Arrhythmias," J. Electrocardiology, vol. 3, No. 3-4, 1970, pp. 251-257.

Medina-Ravell, V, et al., "Management of Tachyarrhythmias With Dual-Chamber Pacemakers," Pace, vol. 6, No. 2, Mar.-Apr. 1983, Part II, pp. 333-345.

Medina-Ravell, V, et al., "Use of Dual-Demand AV Sequential (DVI, MN) Pacemakers in the Management of Supraventricular Tachycardias," Pacemaker Therapy, L. Dreifus ed., 1983, pp. 227-238.

Medtronic Model 5330 A-V Sequential Demand Pulse Generator, Technical Manual, Jun. 1978.

Miyazawa, K, et al., "Effects of Varying Pacemaker Sites on Left Ventricular Performance," Tohoku J. exp. Med., 1976, 120, pp. 301-308.

Miyazawa, K, et al., "Regional Contraction Patterns of the Left Ventricle during Ventricular Pacing," Tohoku J. exp. Med. 1977. 122; pp. 167-174.

Moss, AJ et al., "Atrial Pacing from the Coronary Vein: Ten-Year Experience in 50 Patients with Implanted Pervenous Pacemakers," Circulation, vol. 57, No. 1, 1978, pp. 103-106.

Nelson, GS, et al. "Left Ventricular or Biventricular Pacing Improves Cardiac Function at Diminished Energy Cost in Patients With Dilated Cardiomyopathy and Left Bundle-Branch Block," Circulation, vol. 102, 2000, pp. 3053-3059.

Obel, IWP, Physiological Pacing, Pitman Medical, London, 1979.

Ogawa, S, et al., "Hemodynamic Consequences of Atrioventricular and Ventriculoatrial Pacing," Pace, vol. 1, No. 1, Jan.-Apr. 1978, pp. 8-15.

Popovic ZB, et al., "Noninvasive Assessment of Cardiac Resynchronization Therapy for Congestive Heart Failure Using Myocardial Strain and Left Ventricular Peak Power as Parameters of Myocardial Synchrony and Function," J Cardiovasc Electrophys., vol. 13, No. 12, 2002, pp. 1203-1208.

Portillo, B, et al., "Treatment of Drug Resistant A-V Reciprocating Tachycardias With Multiprogrammable Dual Demand A-V Sequential (DVI, MN) Pacemakers," Pace, vol. 5, No. 6, 1982, pp. 814-825.

Prauer, H, et al., "Prolonged Electrostimulation of the Heart Through the Coronary Sinus; Report of Two Cases with Position of the Electrode Confirmed by Autopsy," Thoraxchirugie Vaskulare Chirurgie, 1974, 22, p. 207.

Program of the VIIth World Symposium on Cardiac Pacing, Vienna, May 1-5, 1983, in Schrittmacher: German Journal of Cardiac Pacing, Apr. 1983, listing De Teresa et al., "An Even More Physiological Pacing Changing the Sequence of Ventricular Activation."

Rodriguez Bailon, I, et al., "Some Data for an Unanswered Question: Choosing the Ventricular Electrode Place," Pace, vol. 8, No. 3, Part II, May 1985, p. A-11.

Rogel, S, et al., "Atrioventricular Time Sequence and Myocardial Efficiency," Archives Internationales de Physiologie et de Biochimie, 1973, 81, 833-42.

Romero, L., et al., "Non-Invasive Evaluation of Ventricular Function and Volumes During Atrioventricular Sequential and Ventricular Pacing," Pace, vol. 7, No. 1, Jan. 1984, pp. 10-17.

Silva, "Influencia de la Localizacion de la Estimulacion Electrica Ventricular Sobre la Eficiencia Cardiaca. Estudio Experimental Y Clinico," ["Influence of the Location of the Location of Ventricular Electrical Stimulation on Cardiac Efficiency"), Tesis Doctoral para la Universidad Autonoma De Madrid Facultad de Medicina (Dated 1987) (Spanish with English-Language Translation Attached).

Program of International Congress of Cardiology, Marrakesh, Morocco, Nov. 4, 1988, listing Silva et al, "Biventricular Stimulation: An Approach to Physiologic Cardiac Stimulation."

Silva et al., "Epicardial Biventricular Stimulation Mimicking Activation During Sinus Rhythm. Experimental Study" European Heart Journal, vol. 8, Supp. 2, Sep. 1987, p. 180.

Smyth, et al., "Permanent Pervenous Atrial AV Synchronous and AV Sequential Pacing," Cardiac Pacing, Thalen, H, ed., Van Gorcum: Assen, Netherlands, 1973, p. 145.

Stokes, K, et al., "The Electrode-Biointerface-Stimulation," Modern Cardiac Pacing, Barold, SS, ed., Futura Publishing, 1985, pp. 33-78.

Sutton, R, et al., "The History of Cardiac Pacing," The Foundations of Cardiac Pacing, Futura Publishing, Mt. Kisco, NY, 1991, pp. 319-324.

Young JB, et al; "Combined Cardiac Resynchronization and Implantable Cardioversion Defibrillation in Advanced Chronic Heart Failure: The MIRACLE ICD Trial," JAMA, vol. 238, No. 20, pp. 2685-2694.

(56) References Cited

OTHER PUBLICATIONS

Zaroff, L, et al., "An Implantable Demand Pacemaker," The Annals of Thoracic Surgery, vol. 4, No. 5, Nov. 1967, pp. 463-467.

Zoll, P, "Resuscitation of the Heart in Ventricular Standstill by External Electrical Stimulation," N. Engl. J. Med., vol. 247, No. 20, 1952, pp. 768-771.

Zuckerman, W, et al., "Clinical Applications of Demand Pacing," Annals of the New York Academy of Sciences, vol. 167, No. 2, Oct. 30, 1969, pp. 1055-1059.

Zuckerman, W, et al., "Clinical Experiences With a New Implantable Demand Pacemaker," Am. J. of Cardiology, vol. 20, Aug. 1967, pp. 232-238.

Communication, mailed Jul. 17, 2006, in European Application No. 04755341.7.

Article: Morton M. Mower, M.D., et al., Unusual Petterns of Conduction Produced by Pacemaker Stimuli, pp. 24-28.

Demetrio Sodi-Pallares, et al., "Deductive and Polyparametric Electrocardiography", Instituto Nacional de Cardiologia de Mexico, 1970, 16 pages.

J.A. Armour, et al., "Functional Anatomy of the Interventricular Septum", Cardiology, 1973, 15 pages.

Morton M. Mower, et al., "Unusual Patterns of Conduction Produced by Pacemaker Stimuli", American Heart Journal, vol. 74, No. 1, Jul. 1967, pp. 24-28.

Demetrio Sodi-Pallares, et al., "New Bases of Electrocardiography", C. V. Mosby Company, 1956, 2 pages.

* cited by examiner

Lead 130

Lead 128

Controller
104

Superior Vena Cava
106

Right Atrium
108

SA Node
116

Atrial Lead Branch
132

Atrial Electrode
134

AV Node
118

Right Ventricle Lead Branch
136

Right Ventricle
112

First Right Ventricle Electrode
138

Right Bundle Branch
122

Left Atrium
110

Left Ventricle Lead Branch
142

Left Ventricle Electrode
144

Bundle of His
120

Left Ventricle
114

Purkinje Fibers
126

Left Bundle Branch
124

Heart
102

404

402

METHOD AND APPARATUS FOR INTRACHAMBER RESYNCHRONIZATION

CROSS-REFERENCE TO RELATED APPLICATIONS

This application is a continuation of U.S. application Ser. No. 15/869,807 filed Jan. 12, 2018, which is a continuation of U.S. application Ser. No. 14/206,111 filed Mar. 12, 2014, which is a continuation of U.S. application Ser. No. 10/656, 222 filed Sep. 8, 2003, the entire contents of all of which are incorporated herein by reference.

FIELD OF THE INVENTION

The present invention relates to medical devices, and in particular, to methods and apparatus for controlling contraction of a heart.

BACKGROUND

During a normal heartbeat, the heart contracts in a coordinated fashion to pump blood. In particular, the heart contracts based on rhythmic electrical impulses, which are spread over the heart using specialized fibers. These rhythmic electrical pulses are initiated by the heart's natural pacemaker called the sino-atrial node ("SA node"). The SA node initiates electrical impulses to cause the right and left atria to contract. As the atria contract, the electrical impulses from the SA node propagate to the atrial-ventricular node ("AV node"). The time these impulses take to propagate from the SA node through the AV node is known as the A-V delay. The A-V delay allows the atria to fully contract and fill the ventricles with blood.

The AV node then transmits the impulse, which causes contraction in the right and left ventricles. Blood from the ventricles then flows out of the heart and to the rest of the body. Therefore, the heart relies upon a rhythmic cycle of electrical impulses to pump blood efficiently.

A heart may suffer from one or more cardiac defects that interfere with the rhythmic cycle or conduction of electrical impulses. For example, one known heart condition is an AV block. An AV block inhibits transfer of impulses from the SA node to the AV node, and thus, inhibits or prevents contraction of the right and left ventricles. Other conditions, such as myocardial scarring and bundle branch block, may slow conduction of impulses, and thus, cause the heart to beat in an uncoordinated fashion.

Typically, an artificial pacemaker is installed to treat these cardiac deficiencies. The artificial pacemaker senses impulses from the SA node and then supplies stimulating electrical pulses to cause contraction in chambers of the heart, such as the ventricles. Therefore, an artificial pacemaker may compensate for blocked or slowed conduction of electrical impulses in the heart.

The specialized cardiac fibers in the heart are completely surrounded by a cell membrane. In a given chamber of the heart, at the points where the ends of the individual fibers meet, two individual cell membranes fuse into a single structure. These structures are known as intercalated discs and they provide a strong connection among all of the individual fibers of the heart. Intercalated discs provide bridges of low electrical resistance, and thus, allow for the rapid propagation of electrical signals throughout the heart during contraction. This phenomenon is known as a functional syncytium.

Since adjacent cardiac fibers in a chamber of the heart normally form a functional syncytium, known artificial pacemakers include only a single electrode in each chamber. Known artificial pacemakers thus rely on the functional syncytium to propagate a stimulating electrical pulse throughout a chamber, even though the stimulus originates from a single electrode.

However, there are cardiac deficiencies that may interfere with the proper contraction within a particular chamber. For example, a chamber may suffer from a defect or injury that blocks the propagation of electrical impulses within the chamber or prevents a portion of the chamber from contracting in a coordinated fashion with other chambers of the heart. As another example, patients with congestive heart failure (CHF) may experience sufficient asynchrony within a single chamber of the heart that the chamber is unable to properly pump blood within a normal rhythmic cycle.

Previously, treatment by stimulating right and left ventricles at the same or similar times has assisted in treating asynchrony. Unfortunately, known artificial pacemakers cannot completely compensate for asynchrony within a single chamber. As noted above, known artificial pacemakers only apply stimulating pulses to a single location within a given chamber using only one electrode. Accordingly, it would be desirable to provide methods, apparatus, and systems, which can overcome these and other deficiencies in the prior art, for example, to assist any given chamber of the heart to contract in a much more coordinated fashion, and thus, assist the heart in contracting more efficiently as a whole in a coordinated fashion. In addition, it would be desirable to provide methods, apparatus, and systems, which can stimulate multiple sites in a chamber of the heart, such as the left ventricle.

SUMMARY OF THE INVENTION

In accordance with an aspect of the present invention, methods and apparatus are provided for controlling contraction of a heart. Signals indicating the electrical activity of sinus rhythm are received from at least a portion of the heart. The progress of contraction in a single chamber of the heart is determined based on the received signals. Alternatively, the progress of contraction of the entire heart or a portion of the heart is determined based on the received signals. The heart is then stimulated at a plurality of locations in a single chamber based on the progress of contraction in the chamber, the entire heart, or other portion of the heart.

In accordance with another aspect of the present invention, a system comprises at least one sensing element, a processor, and a signal generator. The sensing element is configured to receive signals that indicate electrical activity of sinus rhythm of the heart. The processor is coupled to the sensing element and is configured to determine the progress of contraction in the heart based on the received signals. In addition, the processor provides one or more control signals to initiate stimulation of the heart. The signal generator is coupled to the processor, receives the one or more control signals, and is configured to provide at least one signal to stimulate a plurality of locations in the chamber of the heart.

In another embodiment, a plurality of electrodes are implanted in the left ventricle to stimulate at multiple locations in the left ventricle for the purpose of improving hemodynamic performance and increasing cardiac output in a patient who is suffering from congestive heart failure. Electrodes may be implanted in the interventricular septum, in the coronary sinus, in a coronary vein in the left ventricle, in the epicardial wall of the left ventricle, or in any location suitable for stimulating the left ventricle without causing harm to the patient.

Two other techniques for improving cardiac output may also be used with the system and method of the present invention. First, an anodal or cathodal pre-excitation voltage may be applied to pre-condition a portion of the heart. Second, a field stimulation pulse of increased current (on the order of approximately 10 milliamps) may also be applied to improve cardiac output.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate embodiments of the invention and together with the description, serve to explain the principles of the invention. In the figures.

DESCRIPTION OF THE EMBODIMENTS

Methods, apparatus, and systems are provided to control contraction of the heart. At least one sensing element receives signals indicating electrical activity of sinus rhythm of the heart. Based on the received signals, the progress of contraction in a chamber of the heart is determined. Alternatively, the progress of contraction in a portion of the heart or across the entire heart is determined. As explained further below, the progress of contraction may be determined by sensing at multiple electrodes or even by sensing at a single electrode. Based on the progress of contraction, the chamber of the heart may then be stimulated at a plurality of locations to correct an asynchrony.

Reference will now be made in detail to exemplary embodiments of the invention, examples of which are illustrated in the accompanying drawings. Wherever possible, the same reference numbers will be used throughout the drawings to refer to the same or like parts.

Figure 1:
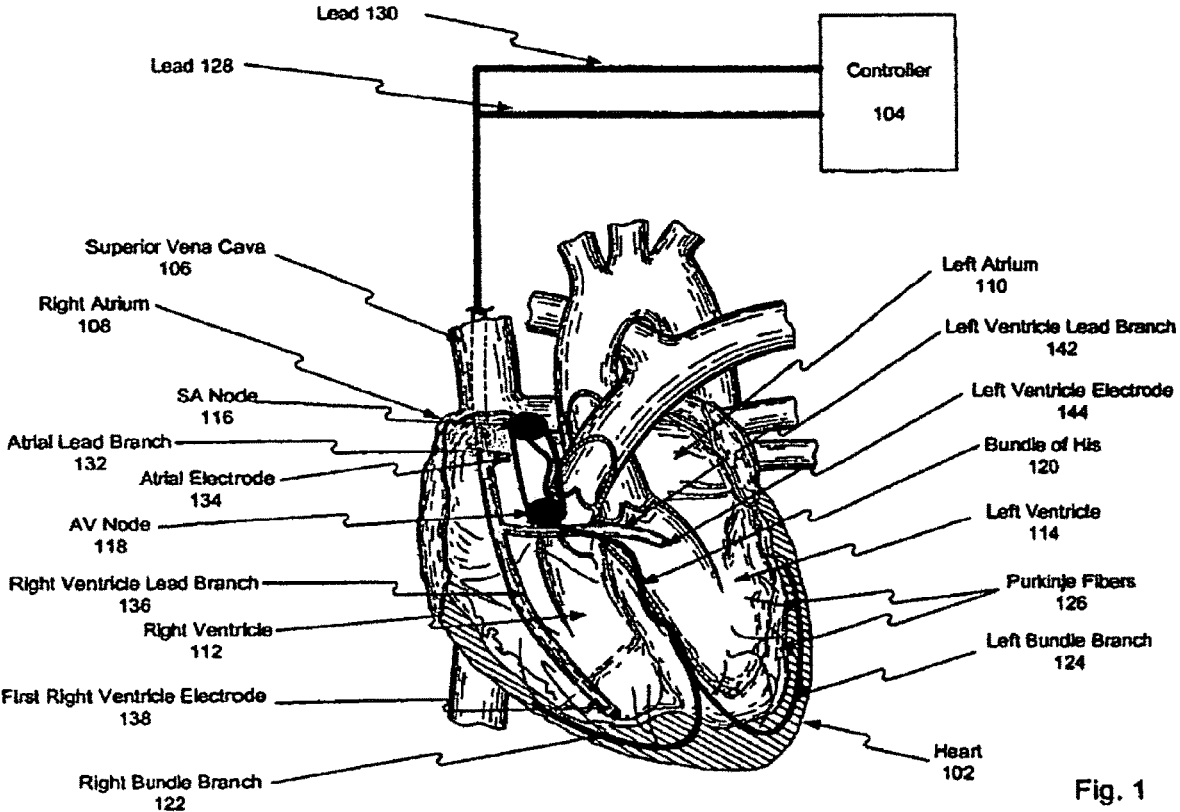
FIG. 1 illustrates an environment in which methods, apparatus, and systems may be applied consistent with the principles of the present invention.

FIG. 1 illustrates an environment in which methods, apparatus, and systems may be applied consistent with the principles of the present invention. As shown, a controller 104 may accompany a heart 102. In addition, heart 102 is shown with a superior vena cava 106, a right atrium 108, a left atrium 110, a right ventricle 112, a left ventricle 114, a sinoatrial node ("SA node") 116, an atrial-ventricular node ("AV node") 118, a Bundle of His 120, a right bundle branch 122, a left bundle branch 124, and Purkinje fibers 126.

Heart 102 normally contracts in two stages based on sinus rhythm. Sinus rhythm is where heart 102 contracts in response to electrical impulses generated from SA node 116. In order to cause contraction in the cardiac muscle of heart 102, the electrical impulses from SA node 116 must depolarize the muscle fibers above a threshold voltage of approximately −80 mV.

Accordingly, as the electrical impulses propagate from SA node 116 to AV node 118, right atrium 108 and left atrium 110 contract. Typically, the electrical impulses take approximately 120 to 200 milliseconds to travel from SA node 116 to AV node 118 and allow right ventricle 112 and left ventricle 114 to fill with blood.

Once the electrical impulses propagate to AV node 118, it then emits another electrical impulse. This electrical impulse propagates relatively quickly over heart 102 down Bundle of His 120, and over right bundle branch 122, left bundle branch 124, and Purkinje fibers 126. In response, cardiac muscles in right ventricle 112 and left ventricle 114 depolarize and contract to pump blood to the rest of the body (not shown).

Controller 104 assists heart 102 to contract in a coordinated fashion based, for example, on sinus rhythm. For example, controller 104 may monitor the progress of contraction in a chamber of the heart 102, such as right ventricle 112 or left ventricle 114, based on analyzing the propagation of electrical impulses throughout heart 102. If controller 104 detects an improper progress of contraction in a chamber, then controller 104 may selectively or automatically stimulate a plurality of locations in that chamber by using a plurality of implanted electrodes.

In particular, controller 104 may be coupled to heart 102 through leads 128 and 130. Leads 128 and 130 may be installed endocardially into heart 102 via superior vena cava 106 using known surgical procedures. Other known surgical procedures include shallow and deep insertions into the coronary sinus, which contains heart 102, septal puncture, sub-xiphoid intra-pericardial insertion, or a thoracotomy. Leads 128 and 130 may be implemented within one or more hollow catheters made of an insulating material, such as silicone rubber, and provide a plurality of connection paths for carrying signals representing electrical activity of heart 102 and carrying electrical signals, such as electrical pulses, from controller 104. For example, lead 128 may further include an atrial lead branch 132, an atrial electrode 132, a right ventricle lead branch 136, a first right ventricle electrode 138, a left ventricle lead branch 142, and a left ventricle electrode 144. Lead 130 may include a second right ventricle electrode (not shown). Alternatively, leads 128 and 130 may be implemented as an integrated lead within a single catheter having multiple, internal connection paths.

In addition, although controller 104 as shown is coupled to two electrodes implanted in right ventricle 112, controller 104 may be implemented with any number electrodes in any chamber of heart 102. For example, methods and systems consistent with the present invention may include two or more electrodes implanted in right ventricle 112 and two or more electrodes implanted in left ventricle 114. One skilled in the art will recognize that the number of electrodes and their placement may depend on the therapy desired. For example, the therapy desired may be evaluated based on electrical criteria, such as p-wave duration, wall-motion of chambers of heart 102, or parameters indicating hemodynamic efficiency of heart 102, such as filling pressure of right atrium 108.

In one embodiment, electrodes may be implanted in heart 102 to form an axis across a chamber of heart 102, such as right ventricle 112 or left ventricle 114. For example, right ventricle electrodes 138 and 140, may be implanted in right ventricle 112 to form a short (or horizontal) axis across right ventricle 112. Alternatively, electrodes 138 and 140 may be implanted in right ventricle 112 to form a long (or vertical) axis across right ventricle 112.

In another embodiment, electrodes may be implanted in heart 102 to surround a chamber of heart 102, such as left ventricle 114. In order to surround the chamber with a relatively few number of electrodes, the electrodes may be placed at relatively equidistant points from each other. For example, right ventricle electrode 138 may be implanted high in the coronary os and right ventricle electrode 140 may be implanted low (or deep) near the apex of right ventricle 112 and the septum between right ventricle 112 and left ventricle 114. In addition, left ventricle electrode 144 may be implanted in the coronary sinus of heart of 102. Although three electrodes are described above, one skilled in the art would also recognize that any number of electrodes may be used in accordance with the principles of the invention. In addition, one skilled in the art would also recognize that the electrodes may be placed at a variety of locations in heart 102.

Atrial lead branch 132 provides a connection path between controller 104 and right atrium 108 for carrying signals associated with right atrium 108 and SA node 116 and electrical signals from controller 104. Although atrial lead branch 132 is shown integrated within lead 128, atrial lead branch 132 may also be implemented using a separate lead from controller 104.

Atrial electrode 132 senses electrical activity in heart 102 associated with right atrium 108 and SA node 116 and delivers electrical signals from controller 104. Atrial electrode 132 may be implemented, for example, as a helical coil of wire made of a metal, such as stainless steel. Although a single electrode is shown, a plurality of electrodes may be implemented with atrial electrode 132.

Right ventricle lead branch 136 provides a connection path for carrying signals associated with right ventricle 112 and providing electrical signals from controller 104 to right ventricle 112. Although right ventricle lead branch 136 is shown integrated within lead 128, right ventricle lead branch 136 may also be implemented using a separate lead from controller 104.

First right ventricle electrode 138 senses electrical activity in heart 102 associated with a location in right ventricle 112, such as electrical impulses from AV node 118 and propagating over right bundle branch 122. Right ventricle electrode 138 may also be implemented, for example, as a helical coil of wire made of a metal, such as stainless steel. In addition, a plurality of electrodes may be implemented with right ventricle electrode 138.

Second right ventricle electrode 140 also senses electrical activity in heart 102 associated with another location in right ventricle 112, such as electrical impulses from AV node 118 and propagating over right bundle branch 122. Second right ventricle electrode 140 may also be implemented, for example, as a helical coil of wire made of a metal, such as stainless steel.

Left ventricle lead branch 142 provides a connection path for carrying signals associated with left ventricle 114 and providing electrical signals from controller 104 to left ventricle 114. Although left ventricle lead branch 142 is shown integrated within lead 128, left ventricle lead branch 142 may also be implemented using a separate lead from controller 104.

Left ventricle electrode 144 senses electrical activity in heart 102 associated with left ventricle 114, such as electrical impulses from AV node 118 and propagating over left bundle branch 124. Left ventricle electrode 144 may also be implemented, for example, as a helical coil of wire made of a metal, such as stainless steel. In addition, a plurality of electrodes may be implemented with left ventricle electrode 144. Moreover, a second electrode may be provided for sensing electrical activity in another portion of left ventricle 114.

Figure 2:
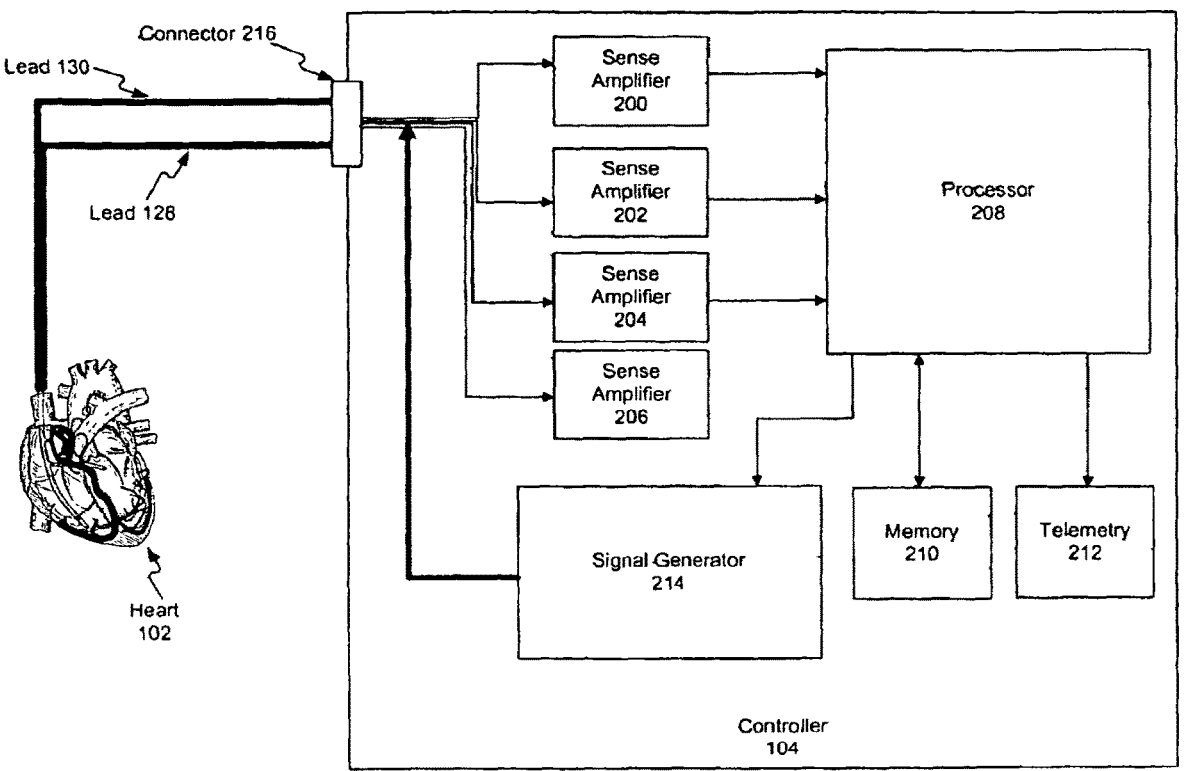
FIG. 2 illustrates a functional block diagram of a controller for controlling contraction of a heart consistent with the principles of the present invention.

FIG. 2 illustrates a functional block diagram of controller 104 for controlling contraction of heart 102 consistent with the principles of the present invention. As shown, controller 104 includes sense amplifiers 200, 202, 204, and 206, a processor 208, a memory 210, a telemetry module 212, and a signal generator 214.

Sense amplifiers 200, 202, 204, and 206 are coupled to atrial electrode 132, first right ventricle electrode 138, left ventricle electrode 144, and second right ventricle electrode 140, respectively via leads 128 and 130. Sense amplifiers 200, 202, 204, and 206 receive signals indicating electrical activity of heart 102 from their respective electrodes, amplify these signals, and provide them to processor 208. Sense amplifiers 200, 202, 204, and 206 may be implemented using, for example, well known circuitry.

Processor 208 receives and monitors signals from sense amplifiers 200, 202, 204, and 206 and generates one or more control signals. For example, in order to monitor the progress of contraction in right ventricle 112, processor 208 may monitor the signals from sense amplifiers 202 and 206 to detect when the electrical activity of heart 102 indicates asynchrony in right ventricle 112.

Processor 208 may detect asynchrony based on a variety of parameters. For example, processor 208 may monitor the electrical activity of heart 102 during sinus rhythm and detect when the electrical activity sensed from second right ventricle electrode 140 fails to reach a threshold level within a predetermined period of time of sensing electrical activity from first right ventricle electrode 138. Processor 208 may be configured to then provide one or more control signals to initiate a stimulating pulse at second right ventricle electrode 140. Processor 208 may use other parameters and values consistent with the principles of the present invention, for example, to treat other conditions. Processor 208 then provides one or more control signals to signal generator 214 based on the electrical activity of heart 102.

Alternatively, processor 208 may be configured to provide one or more control signals to signal generator 214 automatically. For example, upon detecting electrical activity from first right ventricle electrode 138, processor 208 may be configured to provide one or more control signals to initiate a stimulating pulse at second right ventricle electrode 140 after a predetermined delay.

Processor 208 may be implemented using known devices. For example, processor 208 may be implemented using a series of digital circuits or logic gates. Alternatively, processor 208 may be implemented using a microprocessor, such as those manufactured by Intel Corporation.

Memory 210 provides storage for information used by processor 208. For example, memory 210 may include instructions for configuring processor 208 and instructions for monitoring the electrical activity of heart 102. Memory 210 may be implemented using known types of memory, such as a random access memory and read-only memory.

Telemetry module 212 provides diagnostic information indicating the performance of controller 104. For example, telemetry module 212 may transmit the signals received from sense amplifiers 200, 202, 204, and 206 and signals generated by signal generator 214 via a radio link to another device, such as an external programmer (not shown). Telemetry module 212 may also collect and transmit other types of information. Telemetry module 212 may be implemented as a radio receiver/transmitter using a known radio frequency, such as 100 kHz.

Signal generator 214 generates electrical pulses for treating heart 102 via leads 128 and 130. Signal generator 214 may direct electrical pulses to one or more sites in heart 102, such as in right ventricle 112 or left ventricle 114. For example, signal generator 214 may direct one or more electrical pulses to right ventricle 112 through first right ventricle electrode 138 and second right ventricle electrode 140.

Signal generator 214 may generate one or more electrical pulses to assist contraction in heart 102 and compensate for an improper progress of contraction, such as from asynchrony in right ventricle 112. In particular, signal generator 214 may generate one or more electrical pulses using conventional circuitry, such as "one-shot" circuitry. In addition, based on the one or more control signals from processor 208, signal generator 214 may selectively or automatically deliver electrical pulses to electrodes 134, 138, 140, and 144. For example, signal generator 214 may send an electrical pulse to first right ventricle electrode 138, but withhold sending of an electrical pulse to second ventricle electrode 140, and vice versa. Alternatively, signal generator 214 may be configured to deliver electrical pulses automatically to each of electrodes 134, 138, 140, and 144 simultaneously or based on a timing sequence.

In order to stimulate contraction, signal generator 214 may provide a cathodal pulse of 5 V for a duration of approximately 2 milliseconds to electrodes 134, 138, 140, and 144 to stimulate contraction in heart 102. Signal generator 214 may use other types of pulses, such as biphasic pulses or anodal pulses, to stimulate contraction in heart 102. Signal generator 214 may also vary the electrical pulses delivered to each of electrodes 134, 138, 140, and 144. Signal generator 214 may vary the number of pulses, the pulse amplitude, and pulse width. For example, signal generator 214 may vary the electrical pulses delivered based on the desired therapy or effect on heart 102.

Connector 216 provides a connection point for leads 128 and 130. Connector 216 may be implemented using known configurations and components.

Figure 3:
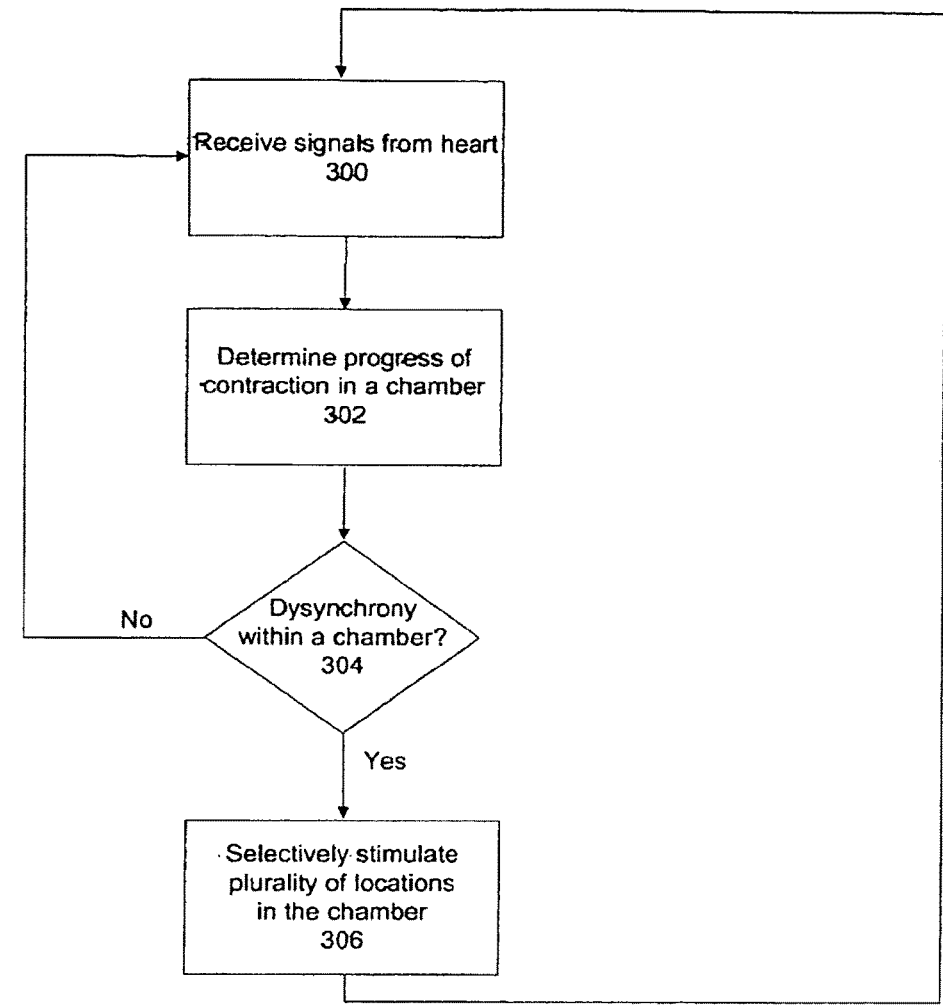
FIG. 3 illustrates a method of controlling contraction of a heart consistent with the principles of the present invention.

FIG. 3 illustrates a method of controlling contraction of a heart consistent with the principles of the present invention. In stage 300, controller 104 receives signals indicating electrical activity of heart 102. For example, atrial electrode 132, first right ventricle electrode 138, second right ventricle electrode 140, and left ventricle electrode 144 may provide signals to sense amplifiers 200, 202, 204, and 206, respectively. Sense amplifiers 200, 202, 204, and 206 may then amplify these signals and provide them to processor 208.

Processor 208 may interpret these signals to determine the electrical activity of sinus rhythm for heart 102. For example, based on signals received from first right ventricle electrode 138 and second right ventricle electrode 140, processor 208 may monitor the progress of contraction in right ventricle 112. In addition, processor 208 may store data from these signals in memory 210, for example, for later transmission by telemetry module 212 to another device.

The system of the present invention can monitor the progress of the contraction across a single chamber and can also monitor the progress of the contraction across the entire heart or a portion of the heart. To rapidly determine the progress of contraction, it is desirable to receive sensing signals from multiple electrodes implanted in various locations across the heart. However, it is also possible to monitor the progress of contraction with only a single electrode. For example, a single electrode in the right atrium can sense when a depolarization occurs in the right atrium. As the depolarization impulse moves into the other chambers of the heart, the single electrode in the right atrium may still be able to sense the subsequent contractions of each successive chamber. For example, the atrial electrode may be able to sense a signal indicating that the left ventricle has contracted—although it the signal will be diminished in magnitude and delayed in time by the time the signal reaches the electrode implanted in the atrium. Thus, the processor will need to account for these factors. The single electrode implanted in the atrium may thus provide sensing signals as each separate chamber contracts, and the progression of the contraction can thereby be monitored with only a single electrode. Similarly, a single electrode could also monitor the progression of a contraction across a single chamber. For example, the electrode may sense a declining ramp in voltage as the depolarization impulse moves away from the electrode. The speed of the decline of the ramp may indicate the speed of the progression of the contraction. The use of multiple electrodes, however, will most rapidly enable the system to effectively determine the progress of the contraction.

In stages 302 and 304, processor 208 determines the progress of contraction in a chamber of heart 102 and detects whether there is asynchrony in the chamber of heart 102. For example, processor 208 may compare the timing of electrical activity indicated in signals from first right ventricle electrode 138 and second right ventricle electrode 140. If the signals from second right ventricle electrode 140 do not reach a threshold level within a period of time of the signals from first right ventricle electrode 138, then processor 208 may interpret this condition as indicating an asynchrony in right ventricle 112 and proceed to stage 306. Accordingly, processor 208 may then generate one or more control signals to assist or resynchronize the contraction of right ventricle 112. In addition, processor 208 may store information related to this event, such as time and amplitude of the event, in memory 210. Alternatively, if processor 208 does not detect any asynchrony in the chamber of the heart 102, then processing repeats again at stage 300.

In stage 306, controller 104 stimulates one or more locations in heart 102, such as one or more locations in right ventricle 112 and/or left ventricle 114. In particular, based on the one or more control signals from processor 208, signal generator 214 may generate and deliver electrical pulses to electrodes 134, 138, 140, and 144. For example, if processor 208 detects asynchrony in right ventricle 112, then processor 208 may generate one or more control signals to command signal generator 214 to deliver electrical pulses to first right ventricle electrode 138 and second right ventricle electrode 140. The pulses delivered to first right ventricle electrode 138 and second right ventricle electrode 140 may be delivered simultaneously or based on a timing sequence. For example, the electrical pulses delivered to second right ventricle electrode 140 may be delayed in comparison to the electrical pulses delivered to first right ventricle electrode 138. Signal generator 214 may control the amount of delay using known techniques and circuitry, such as one-shot circuitry. Processing then repeats again at stage 300.

Figure 4:
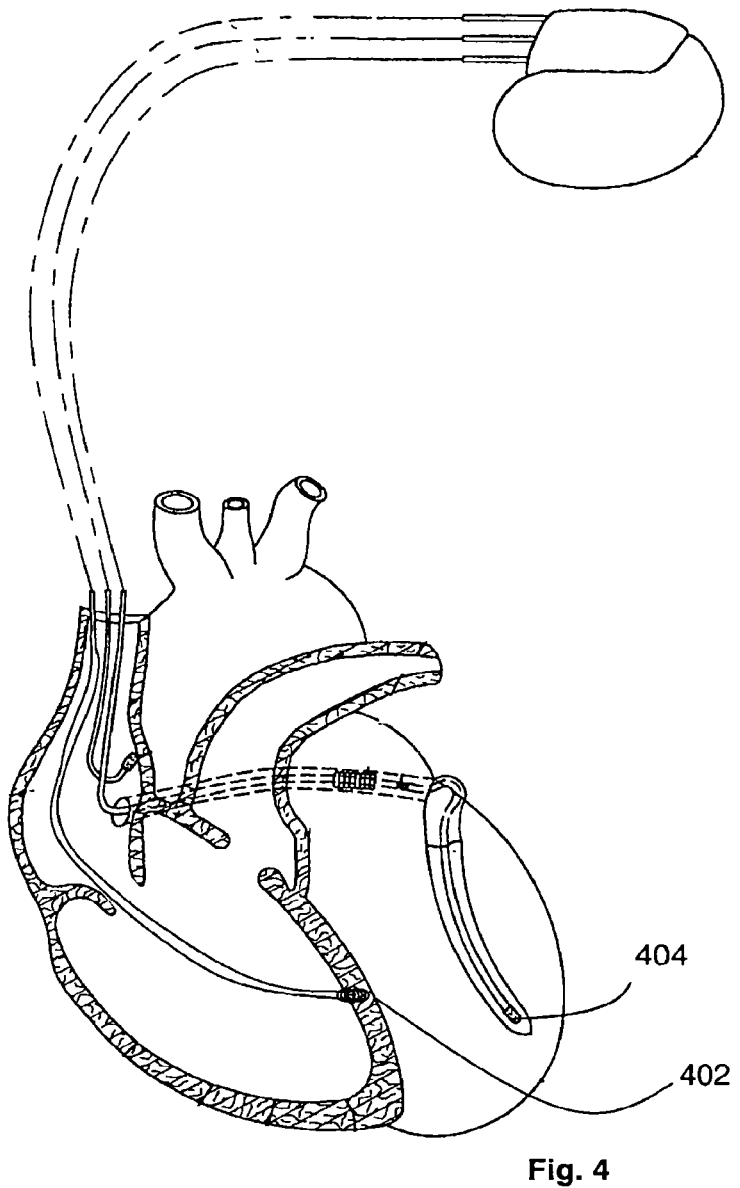
FIG. 4 illustrates an embodiment of the present invention wherein a plurality of electrodes are implanted in the left ventricle.

FIG. 4 illustrates a significant embodiment of the invention that involves stimulating the left ventricle at multiple locations. This embodiment is particularly useful for patients with congestive heart failure (CHF). It has been recognized that patients with CHF can be made to exhibit improved hemodynamic performance by using electrical stimulation to optimize systolic and diastolic function. U.S. Pat. No. 4,928,688 describes an arrangement for achieving bi-ventricular pacing in which electrical stimulating pulses are applied, via electrodes on separate pacing leads, to both the right and left ventricular chambers so as to obtain a coordinated contraction and pumping action of the heart.

More recently, it has been found that pacing only in the left ventricle can produce beneficial hemodynamic results in some circumstances. However, in some of these cases, a single pacing lead in the left ventricle may not be sufficient to produce optimal hemodynamic performance, especially when the left ventricle suffers from conduction defects. In those cases, a system having multiple pacing leads in the left ventricle according to the description below can produce optimal results.

While it is relatively safe to insert a pacing lead and associated electrode(s) into the right ventricle, installing a similar lead into the left ventricle may create a danger to the patient due to the possibility of a thrombus being generated which might result in an ischemic episode. It is therefore important to implant the leads in the left ventricle using a safe method. FIG. 4 illustrates two pacing electrodes 402 and 404 that are designed to be implanted in the left ventricle in a safe manner. Left ventricular pacing electrode 402 may be a helical screw-type electrode. Screw electrode 402 can be approximately 0.375 inches long and may be screwed into the lower portion of the interventricular septum towards the left ventricular wall. This type of pacing electrode, and a method of installing such an electrode, is disclosed in U.S. Pat. No. 5,728,140 to Salo. Left ventricular pacing electrode 402 is screwed in sufficiently so that it stimulates the left ventricular wall.

Left ventricular pacing electrode 404 is advanced through the superior vena cava, the right atrium, the ostium of the coronary sinus (CS), the CS, and into a coronary vein descending from the CS, and is implanted at a desired pacing site in the coronary vein. Alternatively, left ventricular electrode 404 is implanted relatively high in the coronary sinus just within the ostium of the CS.

The ventricular electrodes can alternatively be placed in other locations in the left ventricle. For example, one electrode may be implanted in the interventricular septum, such as pacing electrode 402, and another electrode may be implanted outside of the heart in the epicardial wall of the left ventricle using a screw-in epicardial lead. In another embodiment, one electrode may be implanted in the interventricular septum, and two electrodes may be implanted in the left ventricular epicardial wall—one high up on the epicardial wall nearer the base of the heart, and one lower down on the epicardial wall, nearer the apex. Furthermore, electrode 402 can be implanted to lie even higher or lower in the upper portion of the interventricular septum. For example, as disclosed in U.S. Pat. No. 5,487,758 to Hoegnelid et al., a left ventricular electrode can be passed through the wall of the right atrium and implanted into the upper septum of the superior part of the outer ventricular wall.

Another alternative embodiment is to use two or more screw-in electrodes in the interventricular septum. For example, one electrode could be implanted relatively high on the septum and one lower down on the septum.

Another optional feature that may effectively be used with the system of the present invention is the application of a pre-excitation voltage. A pre-excitation voltage may be applied to either increase or decrease the speed of conduction of a subsequent heart depolarization and the accompanying heart contraction, as will now be further explained.

Before a particular portion of the heart depolarizes and contracts, a pre-excitation voltage may be applied to either increase or decrease the depolarization speed of conduction and contractility of the heart tissue cells in that area of the heart. The pre-excitation voltage is a "sub-threshold" voltage. A sub-threshold voltage is a voltage which is below the threshold stimulus, the minimum strength needed to cause depolarization and contraction of the heart tissue cells.

As mentioned above, a pre-excitation voltage may be applied to heart tissue cells to either speed up or slow down a subsequent depolarization of those cells. To speed up the conduction and enhance contractility of the heart tissue, an anodal (positive polarity) pulse is applied to hyperpolarize the heart tissue cells. On the other hand, to slow down conduction and decrease contractility of the heart tissue, a cathodal pulse (negative polarity) is applied to partially depolarize the tissue cells.

U.S. Pat. No. 6,343,232 to Mower, the inventor of the present invention, discloses augmentation of the electrical conduction and contractility of the heart by biphasic stimulation of muscle tissue. This patent is hereby incorporated by reference. A subthreshold anodal stimulation is applied followed by a cathodal stimulation. The subthreshold anodal stimulation acts as a conditioning mechanism to improve conduction through the heart muscle. A similar concept may be used in conjunction with the system of the present invention.

The mechanism by which pre-excitation affects the speed of conduction and contractility will now be described. Typically, normal heart tissue cells have roughly −90 degrees phase. After the cells are stimulated, an impulse starts traveling down the fiber and the cells shift to an action potential with zero phase. Sick or damaged cells, however, typically do not have −90 degrees phase; they may, for example, have a phase of somewhere in the range of −70 degrees or −80 degrees phase. That is why sick cells conduct slowly. One way to make sick cells conduct faster and more like normal cells that have −90 degrees phase is to artificially enhance the intracellular negativity of the sick cells to −90 degrees phase. If that is done, then when an above-threshold stimulation pulse is applied to depolarize the tissue cells, the cells may have a conduction speed and contractility that is more like a normal cell rather than a sick cell. Even if one were to pre-excite a normal cell and thereby artificially enhance the intracellular negativity to −120 degrees, for example, rather than −90 degrees, the speed of conduction of the cell would become supernormal and result in even more contractility. Thus, the nature of the driven beat depends on the initial electronegativity of the cell, which may be varied by means of pre-excitation.

The decision of whether to use a cathodal or anodal pre-excitation pulse depends on the particular heart condition that is being treated. An anodal pre-excitation pulse is well suited for treating a heart with an asynchrony where one part of the heart is conducting the impulse too slowly (i.e., contracting too slowly). In such a case, an anodal pre-excitation pulse may be applied to hyperpolarize the slowly conducting heart tissue cells, thereby increasing the intracellular negativity of those cells and augmenting conduction in that part of the heart before the depolarization impulse arrives. If an anodal pre-excitation impulse is used to hyperpolarize the tissue, when the tissue later is subsequently stimulated so that it depolarizes, the tissue will depolarize from a more electronegative amount and therefore the phase zero of the action potential and the speed of conduction are increased. Thus, in such a case, the hemodynamic performance of the heart may be improved by the application of an anodal pre-excitation pulse.

A cathodal pre-excitation pulse, on the other hand, may be used to treat a heart condition where it is desired to slow down the conduction of the depolarization impulse. For example, in some hearts, instead of contracting too late, a particular part of the heart may contract too early. This type of event may occur, for example, in patients who have Wolff-Parkinson White syndrome. In some cases, the patient's body automatically pre-excites the heart itself. This may lead to a re-entrant arrhythmia and is undesirable. To treat this kind of condition, a cathodal pulse may be applied to partially depolarize the heart tissue cells in that part of the heart where it is desired to slow down the conduction. By partially depolarizing the tissue, the contractility of the affected area is reduced and the speed of conduction may be delayed or even extinguished by the use of an appropriate cathodal pre-excitation pulse. Thus, the conduction is inhibited in that part of the heart, allowing the rest of the heart to catch up. When the rest of the heart catches up, the inhibition may be released. In other words, the cathodal pre-excitation partially depolarizes the affected tissue cells thereby making the depolarization impulse travel slower and provide a weaker contraction. Thus, the cathodal excitation allows the heart to be resynchronized by inhibiting the conduction speed of the depolarization impulse.

The application of a pre-excitation voltage using the system of the present invention will now be described. First, an electrode senses that the heart has begun to depolarize and contract. Since, the heart begins to contract in the left atrium, an electrode placed in the left atrium will be well-suited to detect the beginning of the heart's contraction. However, an electrode implanted in the right atrium, the right ventricle, or elsewhere in the heart could also be used to detect the beginning of the heart's contraction.

Before the contraction reaches the interventricular septum, a pre-excitation voltage may be applied to the interventricular septum. For example, the pre-excitation voltage may be applied shortly before the right ventricle is predicted to contract or shortly before the left ventricle is predicted to contract. The basic idea is to enhance or inhibit the contractility of the heart tissue cells before the depolarization impulse arrives and before the pre-excited portion of the heart contracts. An anodal voltage may be applied to enhance the speed of conduction, or a cathodal voltage may be applied to inhibit the speed of conduction, depending on the particular heart condition being treated. Alternatively, a pre-excitation voltage could be applied to other areas of the heart besides the interventricular septum, such as at an electrode implanted in the right ventricle or at an electrode implanted in a coronary vein of the left ventricle. Alternatively, a pre-excitation voltage could be applied to multiple electrodes simultaneously. For example, a pre-excitation voltage could be applied simultaneously to electrodes 402 and 404 in the left ventricle, as shown in FIG. 4. For example, if the patient had damaged tissue throughout the left ventricle, an anodal pre-excitation at multiple points in the left ventricle may be effective in speeding conduction through the left ventricle. As another example, as soon as the beginning of the heart contraction is sensed, a pre-excitation voltage could be applied simultaneously to an electrode implanted in the right ventricle, an electrode implanted in the interventricular septum, and an electrode in the coronary ostium above the left ventricle.

The pre-excitation voltage could take the form of a single pulse or multiple pulses. It may have a square pulse shape or it may ramp up and/or ramp down. Potentially, an anodal pre-excitation may be so successful in enhancing conduction that there may be no need to stimulate the heart with an above-threshold stimulation pulse. Thus, as an alternative embodiment, the system may sense whether the contraction progresses sufficiently rapidly with the application of just an anodal pre-excitation voltage, and no above-threshold stimulation. If so, the patient's hemodynamic performance may be optimized by only applying an anodal pre-excitation voltage—there is no need to apply an above-threshold stimulation pulse. If the pre-excitation voltage, by itself, is not sufficient to restore adequate conduction, then the pre-excitation voltage may be followed by an above-threshold stimulation pulse to depolarize the affected area of the heart. More specifically, after the anodal pre-excitation voltage is applied, if a signal indicating that depolarization has occurred is not received from a particular site within a predetermined time, then that site is then stimulated by an above-threshold stimulation pulse.

Thus, as described above, pre-excitation may be used with the system of the present invention to improve resynchronization in a patient with heart failure, thereby improving the cardiac output of the heart.

Another optional feature of that may be used with the present invention to improve resynchronization in a patient with heart failure is the use of "field" stimulation pulses that deliver an increased current. Typically, a conventional pacemaker delivers a current roughly in the range of 3 to 4 milliamps when stimulating the heart. One feature of the present invention is to increase the voltage so that a higher current is delivered, for example, around 10 milliamps.

It has recently been found that if the voltage of the stimulation pulses is increased thereby increasing the current, the resynchronization of the heart tends to improve. The higher amplitude stimulation pulse tends to affect not only the immediate area being stimulated, but also affects the surrounding tissue areas. By delivering a higher current than typically used, the surrounding and distant tissue areas become affected in a manner similar to the application of a pre-excitation voltage. In other words, the higher amplitude stimulation pulse affects the intracellular negativity of surrounding tissue areas. The conductivity of these surrounding areas increases even though the tissue is not completely depolarized immediately upon application of the stimulation pulse. The higher amplitude stimulation pulse pre-conditions the surrounding and distant tissue areas by hyperpolarizing those areas, so that when the depolarization impulse arrives, the conduction speed in those hyperpolarized areas will be increased.

These pulses of increased current are referred to as "field" stimulation pulses because the pulses affect not only the immediate point of stimulation, but they also have an affect on the surrounding field.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of controlling contraction of a heart to improve hemodynamic performance, comprising:

monitoring, with a processing circuit, a progress of contraction in a portion of the heart based on at least a signal received from an electrode implanted in the heart to detect a first condition where the portion of the heart is contracting more slowly than desired or a second condition where the portion of the heart is contracting earlier than desired; and causing a rate of contraction to one of speed up and slow in the portion of the heart by:

generating, with a generator circuit and based on the detection in the progress monitoring, at least one of anodal and cathodal sub-threshold pre-excitation signals, when the first condition is detected, delivering the anodal sub-threshold pre-excitation signal to the portion of the heart, and when the second condition is detected, delivering the cathodal sub-threshold pre-excitation signal to the portion of the heart.

2. The method according to claim 1, wherein the electrode is implanted in the interventricular septum of the heart.

3. The method according to claim 1, wherein the electrode is implanted in the right ventricle of the heart.

4. The method according to claim 1, wherein the electrode is implanted in the left ventricle of the heart.

5. The method according to claim 1, comprising delivering the one of the anodal and cathodal sub-threshold pre-excitation signals to the right ventricle of the heart.

6. The method according to claim 1, comprising delivering the one of the anodal and cathodal sub-threshold pre-excitation signals to the left ventricle of the heart.

7. The method according to claim 1, comprising causing the rate of contraction to speed up.

8. The method according to claim 1, comprising causing the rate of contraction to slow.

9. The method according to claim 1, comprising delivering the one of the anodal and cathodal sub-threshold pre-excitation signals to an electrode implanted in the portion of the heart.

10. The method according to claim 1, comprising delivering the one of the anodal and cathodal sub-threshold pre-excitation signals to more than one electrode implanted in the portion of the heart.

11. The method according to claim 1, comprising stimulating the portion of the heart with an above-threshold stimulating pulse.

12. The method according to claim 1, comprising:

sensing progression of the contraction; and stimulating the portion of the heart with an above-threshold stimulating pulse if the sensing indicates the contraction does not progress sufficiently.

* * * * *